(12) United States Patent
Livchak et al.

(10) Patent No.: US 11,384,941 B2
(45) Date of Patent: Jul. 12, 2022

(54) EXHAUST HOOD

(71) Applicant: Oy Halton Group Ltd., Helsinki (FI)

(72) Inventors: Andrey V. Livchak, Bowling Green, KY (US); Derek W. Schrock, Bowling Green, KY (US); Olli Sipila, Vantaa (FI); Philip J. Meredith, Alvaton, KY (US); Rick A. Bagwell, Scottsville, KY (US); Andrew C. Faller, Smiths Grove, KY (US)

(73) Assignee: Oy Halton Group Ltd., Helsinki (FI)

( * ) Notice: Subject to any disclaimer, the term of this patent is extended or adjusted under 35 U.S.C. 154(b) by 371 days.

(21) Appl. No.: 16/419,456

(22) Filed: May 22, 2019

(65) Prior Publication Data
US 2019/0338958 A1 Nov. 7, 2019

Related U.S. Application Data

(63) Continuation of application No. 14/578,042, filed on Dec. 19, 2014, now Pat. No. 10,634,365, which is a
(Continued)

(51) Int. Cl.
*F24C 15/20* (2006.01)
*F28F 1/24* (2006.01)
(Continued)

(52) U.S. Cl.
CPC .............. *F24C 15/20* (2013.01); *A61L 2/10* (2013.01); *A61L 9/014* (2013.01); *A61L 9/20* (2013.01);
(Continued)

(58) Field of Classification Search
CPC ......... F24C 15/20; F24C 15/2042; F28F 1/24; F28F 1/34; B08B 15/023; B08B 15/00; A61L 2209/16
(Continued)

(56) References Cited

U.S. PATENT DOCUMENTS

| 260,094 | A | 6/1882 | Hankins |
| 888,163 | A | 5/1908 | Hanson |
| | | (Continued) | |

FOREIGN PATENT DOCUMENTS

| AU | 2004202500 A1 | 12/2004 |
| BE | 1009026 | 10/1996 |
| | (Continued) | |

OTHER PUBLICATIONS

European Office Action (Communication under Rule 71(3) EPC) dated Oct. 5, 2020, issued in European Application No. 18168230.3.
(Continued)

*Primary Examiner* — Steven S Anderson, II
*Assistant Examiner* — Phillip Decker
(74) *Attorney, Agent, or Firm* — Potomac Law Group, PLLC; George Dolina

(57) ABSTRACT

An exhaust hood may have an exhaust inlet; a shroud having a lower edge and being movable, the shroud being configured to define an enclosed space over and adjacent a cooking surface, the enclosed space being in communication with the exhaust inlet. The shroud is movable to a first position providing clearance between the cooking surface and the shroud lower edge and a second position providing substantially less than the clearance provided by the first position. A vertical jet at the lower edge is aimed upwardly and along an inside of the shroud when the shroud is in the second position and the vertical jet is in the enclosed space. A horizontal jet is provided at a top of the shroud and aimed along an inside of the shroud when the shroud is in the second position and the vertical jet being in the enclosed space.

10 Claims, 23 Drawing Sheets

Related U.S. Application Data continuation of application No. 12/297,573, filed as application No. PCT/US2007/066853 on Apr. 18, 2007, now Pat. No. 10,473,336.

(60) Provisional application No. 60/745,276, filed on Apr. 20, 2006, provisional application No. 60/745,093, filed on Apr. 18, 2006.

(51) Int. Cl.

| | |
|---|---|
| *F28D 21/00* | (2006.01) |
| *F28C 3/06* | (2006.01) |
| *F28D 15/00* | (2006.01) |
| *B08B 15/02* | (2006.01) |
| *F28F 1/34* | (2006.01) |
| *A61L 9/20* | (2006.01) |
| *B01D 53/00* | (2006.01) |
| *B01D 53/76* | (2006.01) |
| *B01D 53/72* | (2006.01) |
| *A61L 9/014* | (2006.01) |
| *A61L 2/10* | (2006.01) |
| *B08B 15/00* | (2006.01) |

(52) U.S. Cl.
CPC ........... *B01D 53/007* (2013.01); *B01D 53/72* (2013.01); *B01D 53/76* (2013.01); *B08B 15/00* (2013.01); *B08B 15/023* (2013.01); *F24C 15/2042* (2013.01); *F24C 15/2057* (2013.01); *F28C 3/06* (2013.01); *F28D 15/00* (2013.01); *F28D 21/0003* (2013.01); *F28F 1/24* (2013.01); *F28F 1/34* (2013.01); *A61L 2209/14* (2013.01); *A61L 2209/16* (2013.01); *A61L 2209/212* (2013.01); *B01D 2257/7022* (2013.01); *B01D 2258/0275* (2013.01); *B01D 2259/804* (2013.01); *Y02B 30/52* (2013.01)

(58) Field of Classification Search
USPC .......................................................... 454/67
See application file for complete search history.

(56) References Cited

U.S. PATENT DOCUMENTS

| | | |
|---|---|---|
| 1,527,679 A | 2/1925 | Nathaniel |
| 1,611,317 A | 12/1926 | Platte |
| 1,650,859 A | 11/1927 | Florence |
| 2,180,459 A | 11/1939 | Earle |
| 2,532,420 A | 12/1950 | Pledger |
| 2,577,150 A | 12/1951 | Pledger |
| 2,582,884 A | 1/1952 | Nicol |
| 2,608,190 A | 8/1952 | Winning et al. |
| 2,671,440 A | 3/1954 | Dupler |
| 2,746,449 A | 5/1956 | Pledger |
| 2,868,108 A | 1/1959 | Petersen |
| 2,934,913 A | 5/1960 | Haines et al. |
| 3,021,776 A | 2/1962 | Kennedy |
| 3,055,285 A | 9/1962 | Kenneth |
| 3,233,606 A | 2/1966 | Robert et al. |
| 3,242,652 A | 3/1966 | Arthur |
| 3,292,525 A | 12/1966 | Jensen |
| 3,323,439 A | 6/1967 | Weaver et al. |
| 3,358,579 A | 12/1967 | Francois |
| 3,386,365 A | 6/1968 | Jensen |
| 3,410,195 A | 11/1968 | King |
| 3,494,112 A * | 2/1970 | Deckas ................. B08B 15/023 55/470 |
| 3,559,636 A | 2/1971 | Marino |
| 3,564,989 A | 2/1971 | Williams et al. |
| 3,785,124 A | 1/1974 | Gaylord |
| 3,786,739 A | 1/1974 | Wright et al. |
| 3,791,370 A | 2/1974 | Fauser |
| 3,800,689 A | 4/1974 | Brown |
| 3,805,685 A | 4/1974 | Carns |
| 3,807,148 A | 4/1974 | Fike et al. |
| 3,854,388 A | 12/1974 | King |
| 3,943,836 A | 3/1976 | Kuechler |
| 3,980,072 A | 9/1976 | Jacobs |
| 4,016,859 A | 4/1977 | Landowski |
| 4,038,056 A | 7/1977 | Diachuk et al. |
| 4,089,327 A | 5/1978 | Welsh |
| 4,122,834 A | 10/1978 | Jacobs |
| 4,129,121 A | 12/1978 | Dorius |
| 4,143,645 A | 3/1979 | Blumberg |
| 4,175,614 A | 11/1979 | Huggins |
| 4,200,087 A | 4/1980 | Welsh |
| 4,210,429 A | 7/1980 | Golstein |
| 4,345,615 A | 8/1982 | Cicco et al. |
| 4,351,652 A | 9/1982 | Wisting |
| 4,373,509 A | 2/1983 | Neitzel et al. |
| 4,466,420 A | 8/1984 | Emisse et al. |
| 4,475,534 A | 10/1984 | Moriarty |
| 4,483,316 A | 11/1984 | Fritz et al. |
| 4,484,563 A | 11/1984 | Fritz et al. |
| 4,616,562 A | 10/1986 | Kuechler |
| 4,617,909 A | 10/1986 | Molitor |
| 4,738,243 A | 4/1988 | Welsh et al. |
| 4,738,244 A | 4/1988 | Welsh |
| 4,787,920 A | 11/1988 | Richard et al. |
| 4,818,970 A | 4/1989 | Natale et al. |
| 4,825,848 A | 5/1989 | Macias |
| 4,872,892 A | 10/1989 | Vartiainen et al. |
| 4,903,894 A | 2/1990 | Pellinen et al. |
| 4,919,122 A | 4/1990 | Kohlenbrenner |
| 4,934,337 A | 6/1990 | Falk |
| 4,945,891 A | 8/1990 | Cecil |
| 5,042,456 A | 8/1991 | Cote |
| 5,063,906 A | 11/1991 | Rogers et al. |
| 5,069,197 A | 12/1991 | Wisting |
| D327,538 S | 6/1992 | Falk et al. |
| 5,154,161 A | 10/1992 | Rogers et al. |
| 5,205,279 A | 4/1993 | Brown |
| 5,205,783 A | 4/1993 | Dieckert et al. |
| 5,231,972 A | 8/1993 | Galassi |
| 5,251,608 A | 10/1993 | Cote |
| 5,279,279 A | 1/1994 | White |
| 5,285,604 A | 2/1994 | Carlin |
| 5,313,876 A | 5/1994 | Hilger et al. |
| 5,322,473 A | 6/1994 | Hofstra et al. |
| 5,333,601 A | 8/1994 | Hill |
| 5,421,320 A | 6/1995 | Brown |
| 5,467,761 A | 11/1995 | Kuechler |
| 5,475,610 A | 12/1995 | Atwood et al. |
| 5,558,080 A | 9/1996 | Grohman et al. |
| 5,572,984 A | 11/1996 | Alden et al. |
| 5,577,490 A | 11/1996 | Overton, Jr. |
| 5,611,214 A | 3/1997 | Wegeng et al. |
| 5,673,681 A | 10/1997 | Neitzel et al. |
| 5,704,955 A | 1/1998 | Giles |
| 5,845,502 A | 12/1998 | Chen et al. |
| 5,904,751 A | 5/1999 | Niekerk |
| 5,906,195 A | 5/1999 | Georgaras |
| 5,979,429 A | 11/1999 | Schultheis et al. |
| 5,997,397 A * | 12/1999 | Frickel ................. B08B 15/023 312/209 |
| 6,070,655 A | 6/2000 | Heikkila |
| 6,109,257 A | 8/2000 | Hodge et al. |
| 6,125,841 A | 10/2000 | Boudreault et al. |
| 6,170,480 B1 | 1/2001 | Melink et al. |
| 6,173,710 B1 | 1/2001 | Gibson et al. |
| 6,178,966 B1 | 1/2001 | Breshears |
| 6,196,214 B1 | 3/2001 | Niekerk |
| 6,276,358 B1 | 8/2001 | Brin, Jr. et al. |
| 6,308,465 B1 | 10/2001 | Galloway et al. |
| 6,344,074 B1 | 2/2002 | Ward et al. |
| 6,347,626 B1 | 2/2002 | Yi |
| 6,349,716 B1 | 2/2002 | Morton |
| 6,379,240 B2 | 4/2002 | Livchak et al. |
| 6,470,880 B1 | 10/2002 | Chang |
| 6,487,962 B1 | 12/2002 | Horn |
| 6,543,526 B2 | 4/2003 | Jacobs |
| 6,626,971 B1 | 9/2003 | Forbert et al. |

(56) References Cited

U.S. PATENT DOCUMENTS

| | | | |
|---|---|---|---|
| 6,712,063 B1 | 3/2004 | Thorneywork |
| 6,715,484 B2 | 4/2004 | Khosropour et al. |
| 6,752,144 B1 | 6/2004 | Lee |
| 6,802,767 B2 | 10/2004 | Kanaya et al. |
| 6,851,421 B2 | 2/2005 | Livchak et al. |
| 6,869,468 B2 | 3/2005 | Gibson et al. |
| 6,877,506 B2 | 4/2005 | Shekarri |
| 6,878,195 B2 | 4/2005 | Gibson |
| 6,895,955 B2 | 5/2005 | Galassi |
| 6,899,095 B2 | 5/2005 | Livchak et al. |
| 6,945,244 B2 | 9/2005 | Yamada et al. |
| 6,974,375 B1 | 12/2005 | Stevenson et al. |
| 7,001,263 B2 | 2/2006 | Shaben |
| 7,048,199 B2 | 5/2006 | Melink et al. |
| 7,048,625 B2 | 5/2006 | Anezaki et al. |
| 7,147,168 B1 | 12/2006 | Bagwell et al. |
| 7,270,691 B2 | 9/2007 | Arts et al. |
| 7,318,771 B2 | 1/2008 | Huang et al. |
| 7,364,094 B2 | 4/2008 | Bagwell et al. |
| 7,488,919 B2 | 2/2009 | Gagas et al. |
| 7,503,842 B2 | 3/2009 | Lee et al. |
| 7,588,617 B2 | 9/2009 | Kyllönen et al. |
| 7,601,054 B2 | 10/2009 | Bagwell et al. |
| 7,775,865 B2 | 8/2010 | Livchak et al. |
| 7,993,423 B2 | 8/2011 | Kyllönen et al. |
| 8,002,881 B2 | 8/2011 | Bagwell et al. |
| RE42,735 E | 9/2011 | Bagwell et al. |
| 8,038,515 B2 | 10/2011 | Livchak et al. |
| 8,312,873 B2 | 11/2012 | Gagas et al. |
| 8,522,770 B2 | 9/2013 | Colburn et al. |
| 8,872,077 B2 | 10/2014 | Gagas et al. |
| 8,978,324 B2 | 3/2015 | Collins et al. |
| 8,979,959 B2 | 3/2015 | Roughton |
| 9,746,188 B2 | 8/2017 | Worrell |
| 9,874,356 B2 | 1/2018 | Jeong et al. |
| 9,909,765 B2 | 3/2018 | Lyons et al. |
| 10,088,171 B2 | 10/2018 | Lee et al. |
| 2001/0003702 A1 | 6/2001 | Livchak et al. |
| 2001/0039178 A1 | 11/2001 | Elliot |
| 2002/0134371 A1 | 9/2002 | Ward et al. |
| 2002/0162795 A1 | 11/2002 | Pollock |
| 2003/0146082 A1 | 8/2003 | Gibson et al. |
| 2004/0011349 A1 | 1/2004 | Livchak et al. |
| 2004/0014417 A1 | 1/2004 | Katz |
| 2004/0035411 A1 | 2/2004 | Livchak et al. |
| 2004/0118933 A1 | 6/2004 | Readio et al. |
| 2004/0206348 A1 | 10/2004 | Bourassa et al. |
| 2004/0211321 A1 | 10/2004 | Gibson et al. |
| 2004/0242143 A1 | 12/2004 | Gartner et al. |
| 2005/0048896 A1 | 3/2005 | Shaben |
| 2005/0048899 A1 | 3/2005 | Anezaki et al. |
| 2005/0115557 A1 | 6/2005 | Meredith et al. |
| 2005/0229922 A1 | 10/2005 | Magner et al. |
| 2005/0279844 A1 | 12/2005 | Bagwell et al. |
| 2005/0279845 A1 | 12/2005 | Bagwell et al. |
| 2006/0032492 A1 | 2/2006 | Bagwell et al. |
| 2006/0154590 A1 | 7/2006 | Kanaya |
| 2006/0213501 A1 | 9/2006 | Musico |
| 2006/0219235 A1 | 10/2006 | Bagwell et al. |
| 2006/0231553 A1 | 10/2006 | Gerami |
| 2006/0278215 A1 | 12/2006 | Gagas et al. |
| 2007/0015449 A1 | 1/2007 | Livchak et al. |
| 2007/0021046 A1 | 1/2007 | Huang et al. |
| 2007/0021047 A1 | 1/2007 | Huang et al. |
| 2007/0023349 A1 | 2/2007 | Kyllönen et al. |
| 2007/0068509 A1 | 3/2007 | Bagwell et al. |
| 2007/0272230 A9 | 11/2007 | Meredith et al. |
| 2008/0045132 A1 | 2/2008 | Livchak et al. |
| 2008/0196634 A1 | 8/2008 | Pueyo et al. |
| 2008/0207109 A1 | 8/2008 | Bagwell et al. |
| 2008/0302247 A1 | 12/2008 | Magner et al. |
| 2008/0308088 A1 | 12/2008 | Livchak et al. |
| 2009/0032011 A1 | 2/2009 | Livchak et al. |
| 2009/0093210 A1 | 4/2009 | Livchak et al. |
| 2009/0264060 A1 | 10/2009 | Livchak et al. |
| 2010/0005765 A1 | 1/2010 | Kyllonen et al. |
| 2010/0225477 A1 | 9/2010 | Livchak et al. |
| 2010/0229472 A1 | 9/2010 | Malpas |
| 2010/0294259 A1 | 11/2010 | Livchak et al. |
| 2011/0005507 A9 | 1/2011 | Bagwell et al. |
| 2011/0021128 A1 | 1/2011 | Livchak et al. |
| 2011/0053483 A1 | 3/2011 | Ritzer et al. |
| 2011/0094497 A1 | 4/2011 | Schrock et al. |
| 2011/0143648 A1 | 6/2011 | Livchak et al. |
| 2011/0174384 A1 | 7/2011 | Bagwell et al. |
| 2011/0250099 A1 | 10/2011 | Bagwell et al. |
| 2011/0284091 A1 | 11/2011 | Livchak et al. |
| 2013/0113343 A1 | 5/2013 | Singlak et al. |
| 2014/0145566 A1 | 5/2014 | Thompson et al. |
| 2019/0338958 A1 | 11/2019 | Livchak et al. |

FOREIGN PATENT DOCUMENTS

| | | |
|---|---|---|
| CA | 2649712 A1 | 10/2007 |
| CA | 2669486 A1 | 10/2007 |
| CA | 2793796 A1 | 10/2007 |
| DE | 3643299 C1 | 3/1988 |
| DE | 10020205 A1 | 11/2000 |
| DE | 20017731 U1 | 3/2001 |
| DE | 10046537 A1 | 4/2002 |
| EP | 0609740 A1 | 8/1994 |
| EP | 1535538 A1 | 6/2005 |
| EP | 1570765 A1 | 9/2005 |
| EP | 2489943 A1 | 8/2012 |
| FR | 2729004 A1 | 7/1996 |
| GB | 2024392 A | 1/1980 |
| GB | 2298376 A | 9/1996 |
| GB | 2332269 A | 6/1999 |
| JP | S5413444 U | 1/1979 |
| JP | S60138110 U | 9/1985 |
| JP | H01172636 U | 12/1989 |
| JP | H0429752 U | 3/1992 |
| JP | H0735368 A | 2/1995 |
| JP | 2001041554 A | 2/2001 |
| JP | 2004239450 A | 8/2004 |
| JP | 2005007307 A | 1/2005 |
| WO | 0144724 A1 | 6/2001 |
| WO | 0187506 A1 | 11/2001 |
| WO | 2002014728 A1 | 2/2002 |
| WO | 02055935 A2 | 7/2002 |
| WO | 2005019736 A1 | 3/2005 |
| WO | 2005021135 A1 | 3/2005 |
| WO | 2005053830 A2 | 6/2005 |
| WO | 2005114059 A2 | 12/2005 |
| WO | 2006012628 A2 | 2/2006 |
| WO | 2007029173 A1 | 3/2007 |
| WO | 2007121461 A2 | 10/2007 |
| WO | 2007121461 A3 | 11/2008 |
| WO | 2008157418 A1 | 12/2008 |

OTHER PUBLICATIONS

Canadian Office Action for CA Patent Application No. 2,788,491 dated Dec. 8, 2014.
Canadian Office Action for CA Patent Application No. 2,793,796 dated Dec. 8, 2014.
Communication and Extended European Search Report dated Jul. 25, 2012 in European patent application No. 2012160986.
Communication for European Patent Application No. 12160986.1 dated Jun. 26, 2017.
English translation received Apr. 26, 2012, of the second Office Action in Mexican patent application No. MX/a/2008/013396.
English translation received Dec. 13, 2011, of first Office Action in Mexican patent application No. MX/a/2008/013396.
European Office Action dated Mar. 31, 2016 in Application No. 12160986.1-1605.
Extended European search report that issued in the corresponding EP Application No. 18168230.3 dated Aug. 23, 2018.
Office Action dated Aug. 10, 2018 issued in Canadian Patent Application No. 2,965,271.
Office Action for U.S. Appl. No. 14/578,042 dated Jun. 2, 2017.

(56) References Cited

OTHER PUBLICATIONS

Office Action dated Jan. 31, 2012, in Japanese Application No. 2009-506736.
Pre-Examination Report dated Sep. 14, 2018 for Brazilian Patent Application No. PI0710822-2 (with English-language translation).
Requisition by Examiner that issued in the corresponding Canadian Patent Application No. dated Aug. 10, 2018.
Written Opinion of the International Searching Authority for PCT/US2007/066853, dated Jul. 18, 2008.
Office Action (Examiner's Requisition) dated Nov. 6, 2019 for Canadian Patent Application No. 2,965,271.

* cited by examiner

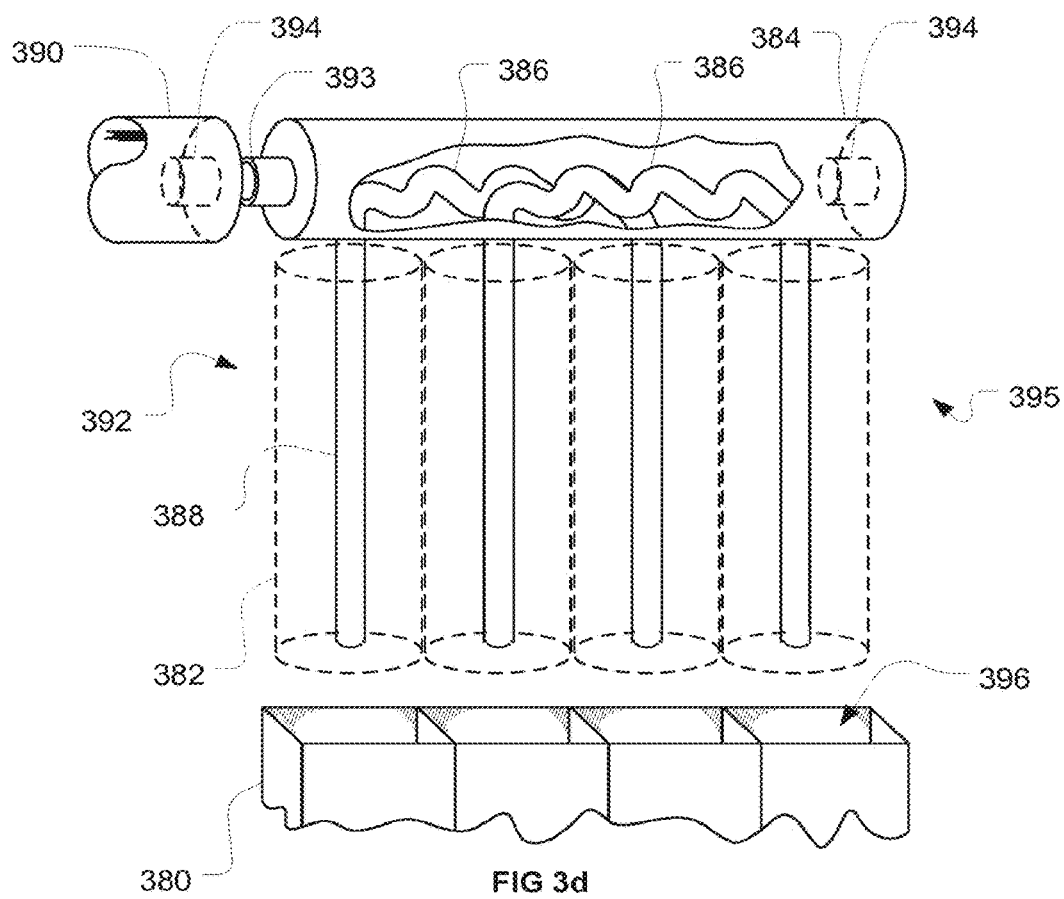
FIG 3d
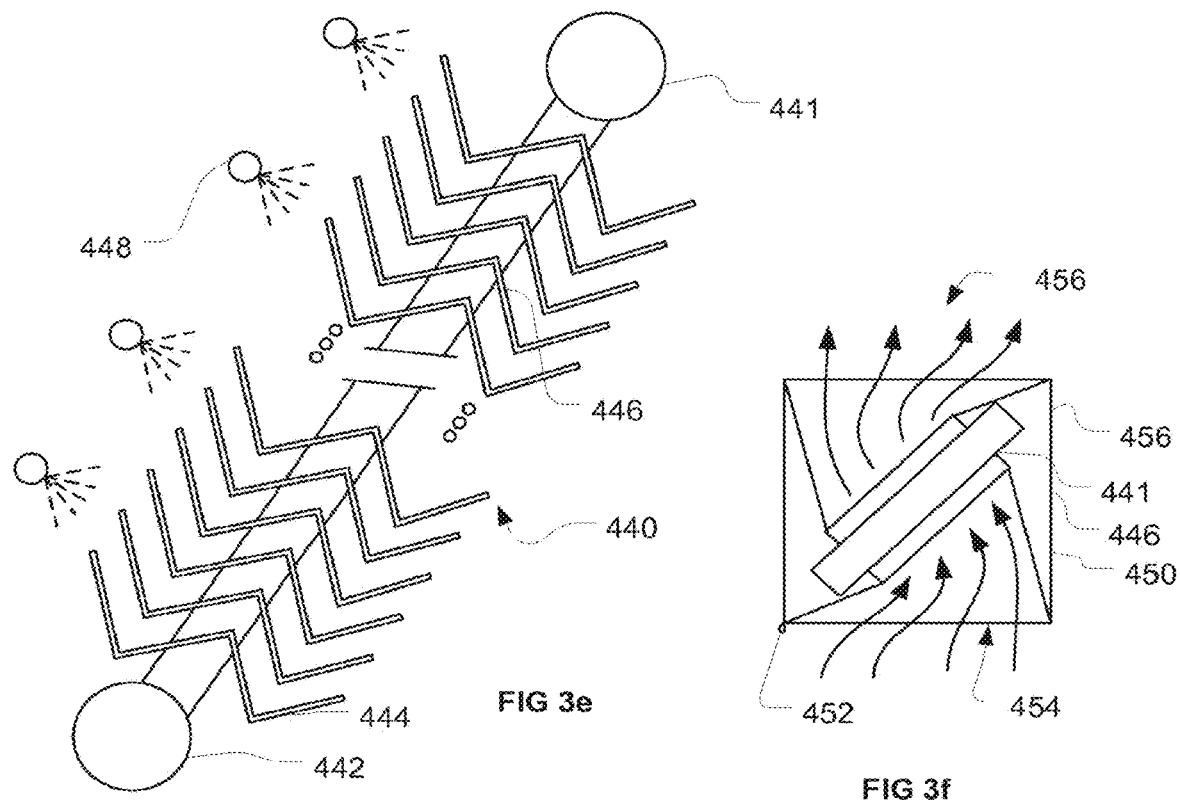
FIG 3e
FIG 3f

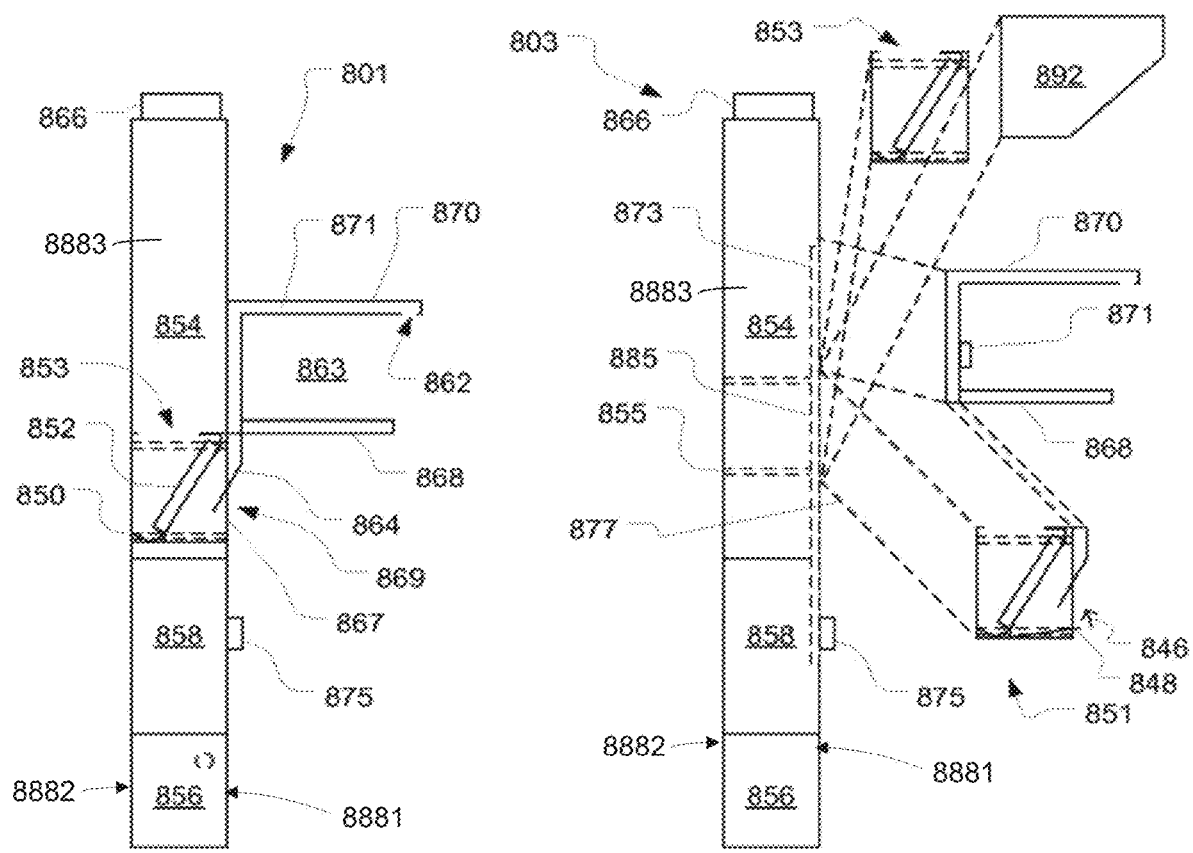
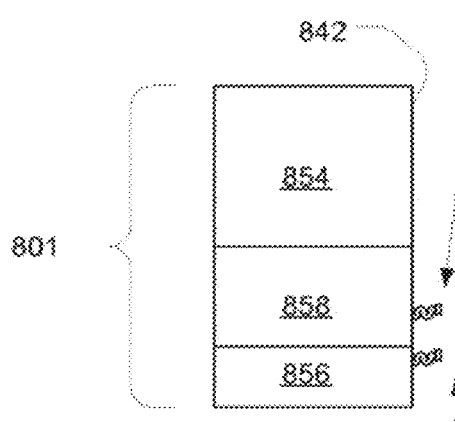
FIG 8a
FIG 8b
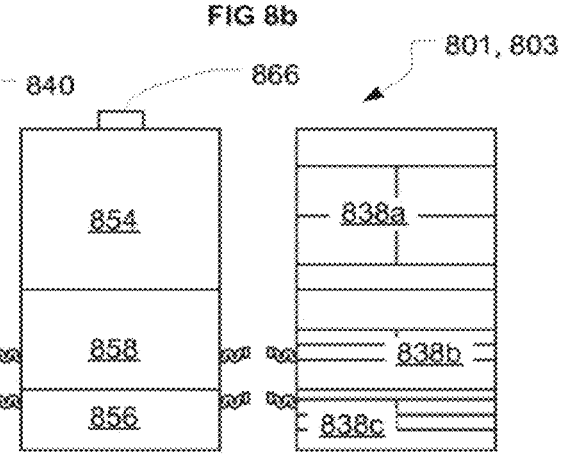
FIG 8c

EXHAUST HOOD

CROSS-REFERENCE TO RELATED APPLICATIONS

The present application is a continuation of U.S. Ser. No. 14/578,042, filed Dec. 19, 2014, which is a continuation of U.S. patent application Ser. No. 12/297,573, filed on Feb. 3, 2009, which is a national stage entry of International Patent Application No. PCT/US2007/066853, filed Apr. 18, 2007, which claims the benefit of priority to U.S. Provisional Application No. 60/745,093 for "RECIRCULATING EXHAUST SYSTEM," filed Apr. 18, 2006 and U.S. Provisional Application No. 60/745,276 for "RECIRCULATING EXHAUST SYSTEM," filed Apr. 20, 2006, both of which have been incorporated by reference in their entirety.

BACKGROUND OF THE INVENTION

Exhaust systems are responsible for a significant loss of energy from industrial and commercial production facilities such as manufacturing facilities, commercial kitchens, laboratories, etc. One of the losses caused by exhaust systems is a result of the withdrawal of significant amounts of conditioned air from the space where contaminants are being produced, which conditioned air must be replaced by conditioning replacement air. Another loss is the energy required to operated exhaust system itself.

As a result of the recognition of a need to minimize the loss of conditioned air through exhaust systems, various technologies have been proposed. One technique is to minimize the volume of conditioned air that is withdrawn. Some exhaust systems operated under pure potential (also known as laminar) flow conditions such as the hoods used in laboratories. By maintaining potential flow conditions, which inherently requires the use of low velocities, mixing of contaminants with is kept to a minimum. The exhaust system can therefore be very selective.

Another approach that has been applied to reduce the quantity of conditioned air lost through exhaust systems is to try to minimize the total flow based on the conditions. For example, real-time control has been described for commercial kitchens. Examples are U.S. Pat. No. 7,048,199 for "Kitchen exhaust optimal temperature span system and method" and U.S. Pat. No. 6,170,480 for "Commercial kitchen exhaust system."

Another approach that has been applied to reduce the quantity of conditioned air lost through exhaust systems is so-called short circuit systems in which make-up air is discharged into the conditioned space close to, or adjacent to, the exhaust hood. The supposed effect of this is to reduce the total volume of conditioned air that must be exhausted while preventing the escape of pollutants into the conditioned occupied space. Examples of such systems are provided by U.S. Pat. No. 4,143,645 for "Self-contained exhaust hood with heat exchanger and method of exhausting air," U.S. Pat. No. 6,347,626 for "Ventilation system for a kitchen," U.S. Pat. No. 4,483,316 for "Air ventilation system." and U.S. Pat. No. 4,483,316 for "Air ventilation system." These systems, however, because the movement of air is inherently turbulent below the hood and around it, vigorous mixing occurs and hoods. As a result, contaminants enter the conditioned air, often more vigorously because of the turbulence generated by the make-up air discharge, and thus, the exhaust hoods are largely required to exhaust as much conditioned air as in systems where make-up air is introduced remote from the hood.

In addition to the loss of conditioned air, and the concomitant need to replace the exhausted air by conditioning replacement air, exhaust system may inherently lose energy or materials that would have commercial value if they could be recovered and used. Because of the dilution of the exhaust stream with conditioned air from the hood environment, however, the concentrations and temperatures are such that energy or material recovery is made difficult. In addition, fouling caused by effluent streams is a performance and maintenance problem for energy recovery systems. For example, heat transfer coefficients of surfaces drop quickly as a result of fouling.

Another issue in the design of exhaust systems is the typical permanence of the configuration once exhaust and utility connections are laid out and installed in a structure. Often it may be desirable to reconfigure a facility such as a commercial kitchen, upgrade appliances and fixtures, or simply relocate equipment. Short circuit exhaust systems offer greater flexibility than those which are connected to outside vents, but utility connections can still pose problems and sometimes short circuit operation is undesirable or impractical in certain facilities.

SUMMARY

The embodiments variously provide features that help to reduce net energy loss in exhaust systems and/or provide for energy recovery.

According to an embodiment, an exhaust hood has an exhaust inlet and a movable shroud. The shroud has a lower edge and is configured to define an enclosed space over and adjacent a cooking surface. The enclosed space is in communication with the exhaust inlet. The shroud is movable to a first position providing at least 20 cm. of clearance between the cooking surface and the shroud lower edge and a second position providing substantially less than the clearance provided by the first position. Preferably, the shroud has a transparent portion. The shroud transparent portion, in an embodiment, is located such that a standing person of average height can view at least a portion of the cooking surface through the transparent portion when the shroud is in the first position. The transparent portion may be located such that a standing person of average height can view at least a portion of the cooking surface through the transparent portion when the shroud is in the first and second positions. Preferably, a fresh air vent is provided in communication with enclosed space. In one preferred embodiment which is suitable for protecting grills, the fresh air vent is configured to form a jet that washes the cooking surface.

According to another embodiment, an exhaust hood has an exhaust inlet and a movable shroud. The shroud has a lower edge and is configured to define an enclosed space over and adjacent a cooking surface. The enclosed space is in communication with the exhaust inlet. The shroud is movable between a first position providing a first clearance between the cooking surface the shroud lower edge and a second position being providing substantially less than the first clearance provided by the first position. In the embodiment, the shroud has a transparent portion. The shroud transparent portion, is preferably located such that a standing person of average height can view at least a portion of the cooking surface through the transparent portion when the shroud is in the first position. The transparent portion may be located such that a standing person of average height can view at least a portion of the cooking surface through the transparent portion when the shroud is in the first and second positions. Preferably, a fresh air vent is provided in communication with enclosed space. In one preferred embodiment which is suitable for protecting grills, the fresh air vent is configured to form a jet that washes the cooking surface.

According to an embodiment, a services supply device for a commercial kitchen has modules which are interconnectable to form a wall. The modules include at least a first module with an exhaust duct where the first module has a gas passage with a holder for a gas filter. The exhaust duct is in flow communication with the gas passage. Preferably, at least a second module has a data bus. Also, preferably, at least one of the first and second modules includes water services piping. Preferably, the modules are connectable to form walls. The modules can be connectable in a stack to form wall sections. Adjacent sections can be connected together to form a continuous wall. The service elements within the modules can be interconnected between adjacent sections to convey services between adjacent sections. Connectors are preferably provided to connect terminal devices to the service conveyances within the walls.

According to an embodiment, a services supply device for a commercial kitchen has modules which are interconnectable to form a wall. The modules include at least a first module including an exhaust duct. The first module has attachments for fixtures including a shelf, a filtration unit, or an exhaust hood.

According to an embodiment, a services supply device for a commercial kitchen has modules which are interconnectable to form a wall. The modules include conveyances that are interconnectable between modules forming the wall so as to convey, between adjacent modules, at least three of data, water, exhaust fumes, drainage, and electrical power. The modules are configured to permit the connection of terminals to the conveyances to provide external access to the services provided by the conveyances.

According to an embodiment, a method of conveying heat energy includes flowing conditioned air into an exhaust hood past a movable partition and flowing the exhaust fumes through a heat exchanger to recover heat in the exhaust fumes.

According to an embodiment, a method of conveying heat energy includes restricting the flow of conditioned air into an exhaust hood by lowering a movable barrier and lowering a flow rate of exhaust through the hood, thereby raising the temperature of exhaust fumes. The method further includes flowing the exhaust fumes through a heat exchanger. Preferably the method also includes conveying heat from the heat exchanger to a consuming process.

According to an embodiment, a method of conveying heat energy includes filtering exhaust fumes from a cooking exhaust hood, passing filtered exhaust fumes through a heat exchanger and conveying heat therefrom to a heat-consuming process. Preferably, the filtering includes exposing the exhaust fumes to ultraviolet light to convert olefins in the exhaust fumes to ash. Preferably, the method includes filtering the ash prior to passing the ultra-violet-filtered flue gas through the heat exchanger.

According to an embodiment, a method of conveying heat energy includes spraying water into a chamber through which exhaust fumes from a cooking exhaust hood are conveyed, collecting water heated by the exhaust fumes and transferring the heat therein using a heat exchanger. In an embodiment, the water contains a surfactant.

According to an embodiment, a method of conveying heat energy includes flowing exhaust fumes from an exhaust hood through a heat exchanger and using a liquid conveyed through the heat exchanger as a heat source for a heat pump to generate heat at a higher temperature than the liquid. Preferably, the method further includes using the heat exchanger to collect grease. In embodiments, the heat exchanger includes a water spray or the heat exchanger is a water spray. Preferably, the method includes conveying heat from the heat pump to potable water. Preferably, the method includes, either additionally or alternatively, using heat from the heat pump to pre-heat potable water.

According to an embodiment, a device for extracting heat has a gas flow conduit defining a gas-conveying portion and a filter holder. A spray nozzle is configured to spray a liquid into the first gas-conveying portion. The spray nozzle has connections for a liquid supply. The first gas-conveying portion has a liquid collection opening. Preferably, a filter is held by the filter holder. Preferably, the filter is a substantially planar mesh filter. In one embodiment, the filter is a substantially planar filter having layers of perforated sheeting defining tortuous flow paths therein.

According to an embodiment, a device for extracting heat has a grease extraction element that defines at least one gas flow path that is tortuous and at least one grease collection channel adjacent the gas path. The grease extraction element defines at least one liquid conduit that is/are physically separate from the at least one gas flow path; the at least one gas flow path and the at least one liquid conduit having respective heat transfer surface portions. The at least one liquid conduit heat transfer surface portions are in thermal communication with the at least one gas flow path surface portions such that a heat conduction path is defined therebetween. Preferably, the liquid conduit has at least one fluid inlet and at least one fluid outlet. Preferably, a housing defines gas inlets and outlets and grease collection portions, including a grease collection outlet, configured to convey grease from the grease collection channel to the grease collection opening. Preferably, the at least one gas flow path includes multiple vortex chambers. In an embodiment, brush elements, at least in part, define the gas flow path. The brush elements preferably have bristles and at least one tube supports the bristles. The surfaces of the bristles, in this embodiment, define at least a portion of the at least one gas flow path heat transfer surface. According to another embodiment, the device for extracting heat further includes an exhaust hood with a kitchen appliance positioned under the exhaust hood and there is a duct connecting the exhaust hood to the gas flow path.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 3b illustrates a top view of the heat exchanger and grease extraction filter combination of FIG. 3a.

FIG. 3d illustrates a combination vortex-type grease filter and heat exchanger.

FIGS. 3e and 3f illustrate another embodiment of a combination filter and heat exchanger.

FIG. 5b is a front-on view of the embodiment of FIG. 5a.

FIG. 5c illustrates a control algorithm which may be used to vary the exhaust airflow rate of the non-ventilating hood which may improve the grease removal performance of the system when used over cooking appliances such as a stove, fryer, or grill.

FIGS. 8a-8d illustrate a modular wall system which is used to provide exhaust, fire suppression, utilities, and other services to one or more cooking appliances.

FIG. 8e illustrates a detail of a shelf that helps to conduct effluent into an intake and which is cleanable.

DETAILED DESCRIPTION

In addition to the fouling problem, there is an opportunity cost and a disposal problem associated with the collection of "waste" heat. The heat collected from the heat exchanger can simply be discarded, for example, by sending consumed cooling water into a sewer or transferring heat from a coolant to ambient outdoor air using a liquid-air heat exchanger, or by transferring heat to other heat sinks, such as the earth, natural water bodies, cooling towers, etc. The opportunity associated with this disposal problem includes the re-use of the otherwise wasted materials and enthalpy, for example, grease, which can provide a source for biofuels, and heat. Another opportunity is that cleaning exhaust rather than simply sending into the environment, provides environmental benefits.

One group of applications that motivate the embodiments in the instant specification are those where permanent connection to an exhaust system is either undesirable or impossible. These are so-called closed cycle or recirculating exhaust applications. Another group, which may identify as energy-recovery applications, are those where energy recovery or minimal energy consumption are desired or needed. The two groups are, obviously, not exclusive or coterminous. In systems closed cycle systems, exhaust fumes, which usually include air drawn directly from the surrounding space, may be treated returned to the ambient. This closed cycle may provide an energy recovery effect, such as where a net heat gain is advantageous and the treated fumes serve to heat the ambient air. In energy recovery embodiments, heat may be extracted and used by various means to increase the efficiency of space, water, or other heating applications. Most of the contemplated provide for the substantial removal of contaminants, including heat, before returning exhaust products and air to the, usually-occupied, space.

One application field is commercial kitchens. Avoiding the installation and updating of permanent exhaust systems, including fans and ductwork, within a structure has many benefits in terms of cost, appearance, flexibility, reliability and other factors. In addition, the thorough recovery and use of waste products has obvious environmental and potential economic benefits.

Heat may be captured at low temperatures and re-used as a source of preheating by processes that require higher temperatures or as heat sources for a heat pump that lifts the use temperature using a source of power. Sources that can make use of low temperature heat may make use of recovered heat. Also, heat exchanger design can maximize the recovery temperature, for example, use of counterflow heat exchanger configurations may accomplish this.

Figure 1A:
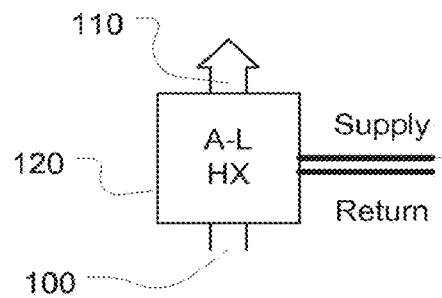
FIG. 1a illustrates a heat exchanger, which may be used as part of a non-venting exhaust device, to cool and clean the effluent stream of a cooking appliance, such as a stove, fryer, or grill.

FIG. 1a illustrates a heat exchanger, which may be used as part of a non-venting exhaust device, to cool and clean the effluent stream of a cooking appliance, such as a stove, fryer, or grill. A stream of warm or hot effluent 100 which consists primarily of smoke, grease, stream, and air from a cooking process and the surrounding environment passes through an air to liquid heat exchanger 120. A liquid line 140 supplies coolant to the air to liquid heat exchanger 120 and conducts heated coolant away. The cooling of effluent 100 by the liquid heat exchanger 120 and the large surface area of the heat liquid heat exchanger 120 help to precipitate grease particulates and the cooling effect helps to condense water vapor on the cooling surfaces of the heat exchanger. After the effluent 100 passes through the heat exchanger 120, much of the grease and heat has been removed. In a simple embodiment, the source for the coolant may be any suitable cold water supply.

In the embodiment of FIG. 1a, heat transfer surfaces cool the exhaust stream, reducing enthalpy, thereby removing moisture. At the same time, if grease aerosols and organic vapors are not removed upstream (as they may be according to further embodiments described below), the heat transfer surfaces may cause grease accumulation (impact filtration) and/or condensation of organic vapors. In any case, fouling is a significant problem which may be addressed by various mechanisms including pre-cleaning the exhaust stream before making contact with the heat transfer surface, periodic or continuous cleaning, use of disposable filter or disposable filter surface, use of a regenerating heat transfer surface, and other means. The further embodiments discuss various ways of accomplishing these.

Figure 1B:
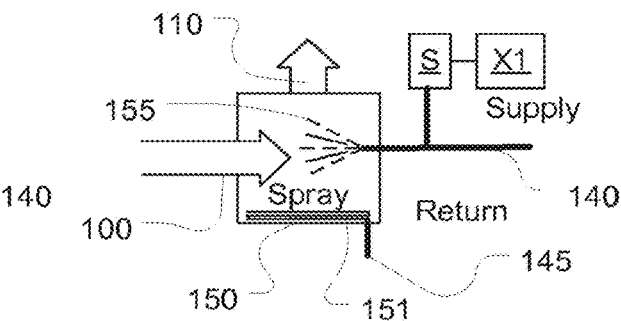
FIG. 1b illustrates another embodiment of a heat exchanger.

FIG. 1b illustrates another embodiment of a heat exchanger. In this embodiment, the cooking effluent 100 passes through a water spray 155. The spray 155 cools the exhaust, and may condense water vapor and organic vapors as well as remove particulate pollutants from the effluent stream 100. Water collects in the chamber 150 as runoff and may be disposed of through a drain 145. Surfactants, grease-eating microbes, other compounds may be automatically supplied at intervals from a reservoir, pump, and control valve (for example, as indicated at S) under control of a controller X1. The controller X1 may be configured to add surfactant according to a regular schedule, continuously, or according to a total cumulative load, to the fluid making up the spray 155. This periodic or continuous addition of surfactant may help to carry away grease in the runoff stream through the drain 145. Heat from runoff water may be captured and re-used. Heat capture may be provided by a heat exchanger 151, for example, a fluid circuit built into the wall as a liner where the runoff accumulates before being discharged through the drain 145. Examples of how captured heat may be used are discussed below.

Figure 1C:
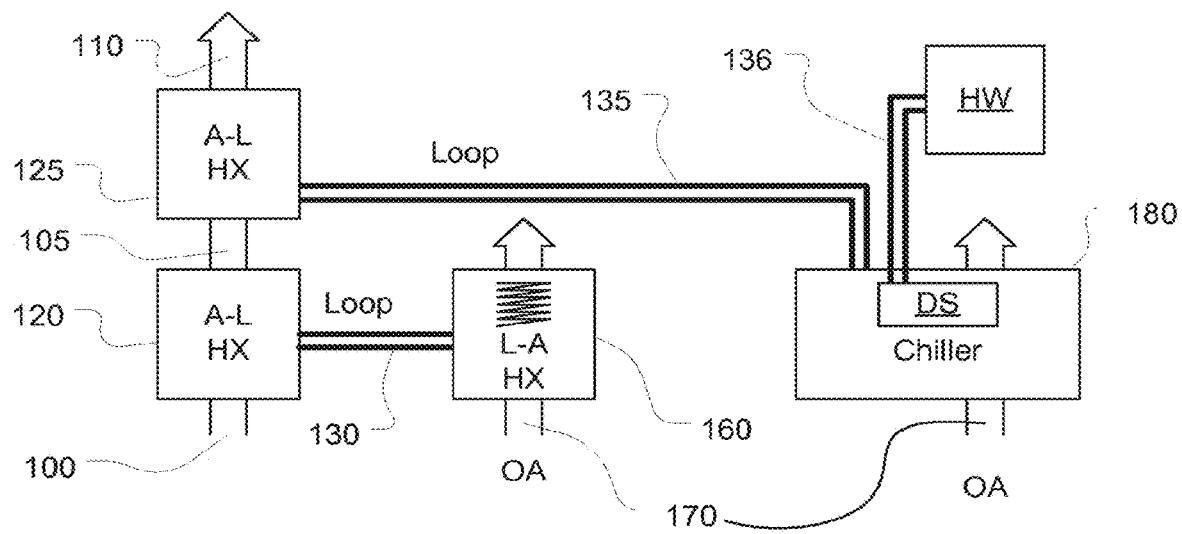
FIG. 1c illustrates a two stage heat exchanger.

FIG. 1c illustrates a two stage heat exchanger. In this embodiment, the effluent 100 first enters a heat reclaim component that includes a heat exchanger 120 with a closed circuit liquid line 130 is used to transfer heat from the liquid-air heat exchanger 120 to another liquid-air heat exchanger 160. The liquid-air heat exchanger 120 removes excess heat from effluent 100 resulting in a partially cooled effluent stream 105. An air to liquid heat exchanger 160 may be used to supply a cooling loop 130 and may also be used to for energy recovery. A second stage cools the effluent stream 105 further resulting in a cooler effluent stream 110. The second stage may employ a second liquid-air heat exchanger 125 whose heat transfer fluid is cooled by chiller 180, for example, a rooftop chiller. Heat may be recovered via closed circuit loop 136 from a desuperheater DS in the chiller to supply heat to a hot water tank HW to handle some portion or all of a hot water load. For example, in a kitchen, the hot water may be used for dishwashing.

Figure 1D:
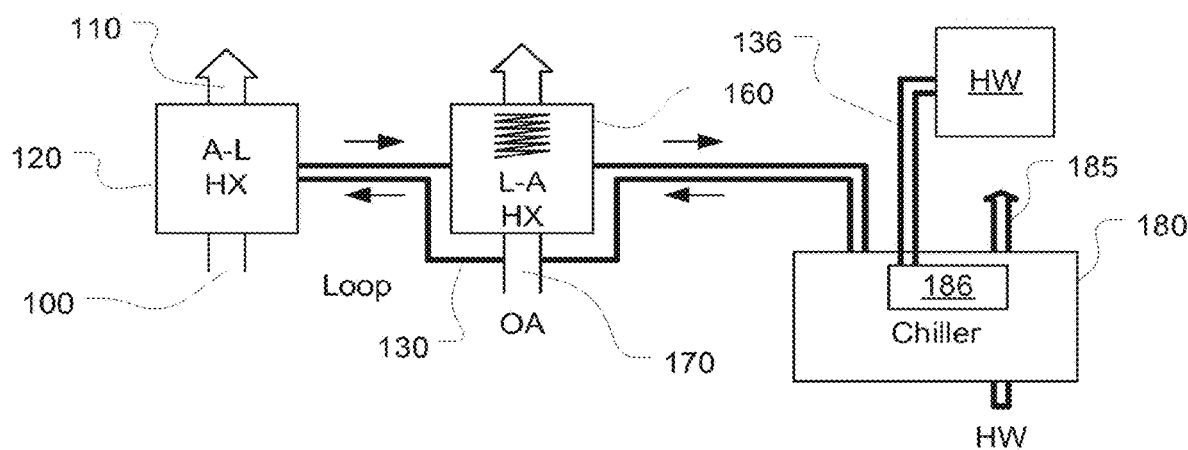
FIG. 1d illustrates another embodiment of a two stage heat exchanger.

FIG. 1d illustrates another embodiment of a two stage heat exchanger. In a first stage, a primary air to liquid-air heat exchanger 120 pre-cools the effluent down to a first final temperature using a relatively high temperature source of coolant such as a liquid-to-air heat exchanger 160 which cools a liquid coolant in a loop 130 using outdoor ambient air 170. In a second stage, a secondary liquid-air heat exchanger 125 further cools the pre-cooled effluent 105 down to a final temperature using a relatively low temperature source of coolant such from a loop 135 connecting the secondary liquid-air heat exchanger 125 to a chiller 180. The second stage may be replaced with a pure refrigerant loop rather than employing an intermediate liquid coolant as in a split air-conditioning system with a similar effect. As in the previous embodiment, heat may be recovered from a desuperheater to pre-heat or heat water. Alternatively, the heat may be recovered by means of a liquid-refrigerant condensing heat exchanger 186 with a desuperheating component. The may be supplemented by an air refrigerant condensing portion (not shown) to provide a heat sink when the hot water load is low.

Figures 1E, 1F:
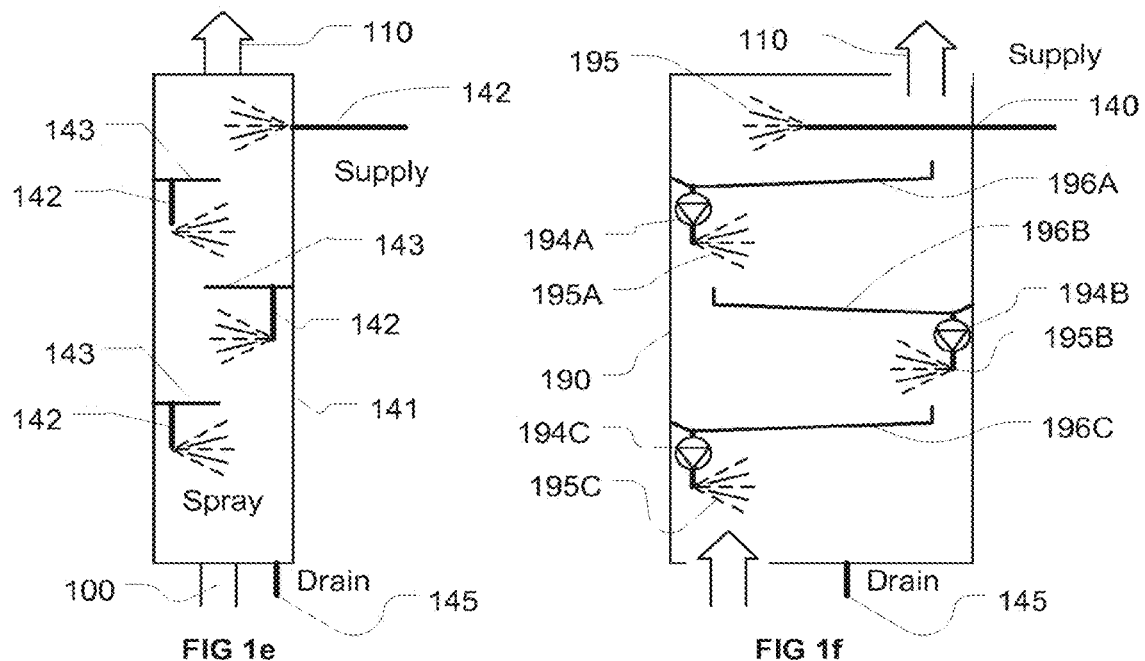
FIGS. 1e and 1f illustrate multi-stage spray cooling systems.

FIG. 1e shows a multi-stage spray cooling system. In this embodiment, the cooking effluent 100 passes into a plenum 141 with multiple spay heads 142 and multiple baffles 143. Runoff from the spray exits through a drain 145. Cleaned 110 air leaves the plenum 141 at an end opposite the inlet.

FIG. 1f illustrates a multi-stage spray cooling system. In this embodiment, the cooking effluent 100 may pass through a series of water sprays 195. If the spray 195 is supplied in a spray chamber 190 at a sufficiently cool temperature, the grease may be condensed or come out of suspension in the effluent stream 100 and the stream 110 which exits the system may be both cooler, cleaner, and dryer. A series of spray nozzles (not shown) may spray cold water into the chamber 190. The runoff from spray 155 may be collected in a collection pan 156A and pumped by a pump 154A though a second spray nozzle 155A. The runoff from spray 155A may be collected in a collection pan 1568 and pumped by a pump 1548 though a third spray nozzle 1558. The runoff from spray 1558 may be collected in a collection pan 156C and pumped by a pump 154C though a fourth spray nozzle 155C. The final runoff may be collected through drain 145 for use (as described in the above embodiments or further embodiments below) or may be disposed of.

In its simplest form, the source for the spray 155 may be a cold water supply. One drawback of this design is that the resulting spray will tend to coagulate and may block the drain lines or coat the inside the spray chamber 150. Detergents, grease-eating microbes, other compounds may be added to the spray 155 to help minimize the problem of grease accumulation in practice. A drain 145 may also be added to drain runoff water. A surfactant may be periodically added to the spray to wash the interior of the chamber as discussed with reference to FIG. 1b. One advantage of this system is that the maximum amount of heat and grease may be removed from the cooking effluent 100 with a minimal amount of water because of the counter-flow effect of the arrangement of nozzles.

Figures 2A, 2B:
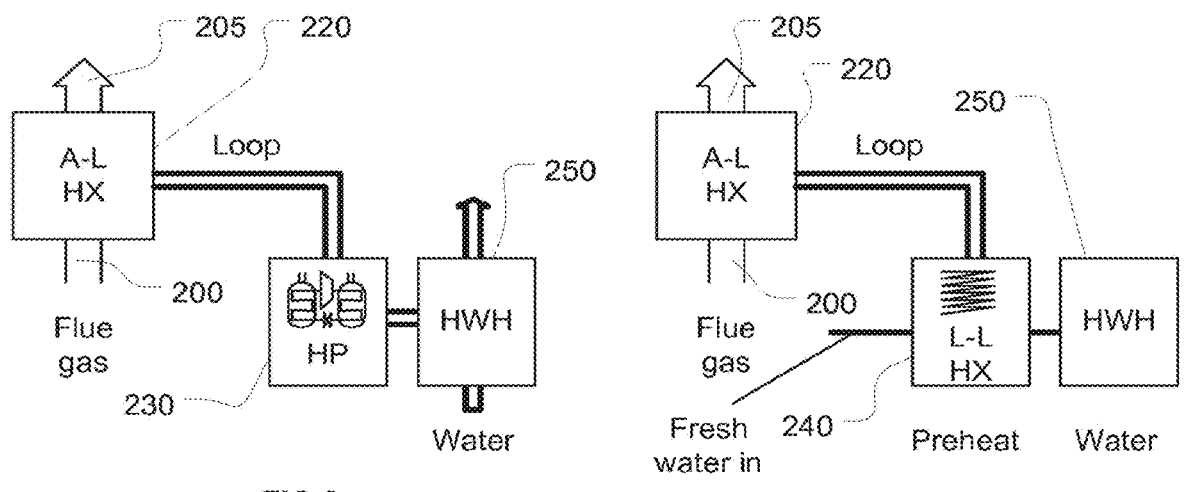
FIG. 2a illustrates a self-cleaning heat exchanger system.
FIG. 2b illustrates a dual-loop heat exchanger system.

FIG. 2a illustrates a self-cleaning heat exchanger system. In this embodiment the grease laden effluent 100 enters an air-liquid heat exchanger 200 in which the effluent is cooled and cleaned resulting in a clean air stream 205. This embodiment utilizes a heat pump 230, which, in normal operation may provide the cooling loop for the heat exchanger 220. Heat may be rejected from the heat pump via a liquid loop connected to a consumer appliance that requires high input temperatures, such as a hot water heater 250. The latter could also be a dishwasher, food warmer, or other appliance which may be found in a commercial kitchen. Reclaimed heat may be so used in any of the embodiments described herein. Reclaimed heat can also be used for pre-heating a fluid such as potable water supplied to a water heater or water provided for dishwashing.

The heat pump cycle may be reversed to provide a temporary heating effect to the heat exchanger 220 which may be used to melt accumulated grease from the heat exchanger surface. The temporary heating effect may be provided when the fume load is low or zero. For example, the fume generating appliance may provide a signal indicating current or future load which may be used to control the application of heating effect. Some batch-type appliances, such as batch fryers, operate on a regular schedule, so controlling to automate the heat pump reverse cycles presents a straightforward control problem, once the task is defined. Most grease filtering devices are provided with a grease collection system. So the embodiment contemplated in connection with FIG. 2a would have a conventional grease collection system configured to collect grease that falls from the heat exchanger (evaporator/condenser coil).

Note that in addition to the above, the embodiment of FIG. 2a may also be equipped with a spray device to clean the heat exchanger periodically to ensure that any grease that does not drip from the heat exchanger during the reverse (heating) cycle will still be removed. This will help to ensure good heat transfer performance. See FIG. 2f, and attending discussion, for a configuration that provides cleaning. The cleaning cycle can also be controlled to occur automatically during non-operating periods based on a timer or based on input from fume generating equipment. In another alternative embodiment, instead of pumping heat from the air-liquid heat exchanger 220 to a hot water heater 250, the heat can be rejected to a heat sink such as outdoor air as in the embodiment of FIG. 2e, described below. In addition, the air-liquid heat exchanger can, in yet another embodiment, be part of a refrigerant loop.

As part of a non-recirculating hood system, an ultra-compact heat pump may be preferred. For example, an absorption-type device such a described in U.S. Pat. No. 5,611,214, hereby incorporated by reference as if set forth in its entirety herein. Such a system may use heat from a heat source that converts the fuel of the heat source to heat, or may extract high temperature heat from the heat source using a heat exchanger attached to the appliance. The heat pump may also obtain high temperature heat from a heat source, such as a waste heat source, other than the fume generating appliance. For example, heat could be collected from an oven vent.

FIG. 2b illustrates a dual-loop heat exchanger system. This embodiment is similar to that of FIG. 1a, but the source of coolant water is a water preheater that provides fresh preheated water to a hot water heater or storage hot water heater or storage tank 250. As in the embodiment of FIG. 2a, the device indicated at 250 may be a preheated storage tank for use with a tankless water heater or a hot water heater. An intermediate heat exchanger 240 provides an additional layer of security against contaminant breakthrough. The liquid-liquid heat exchanger transfers heat between the air liquid heat exchanger 220 and the hot water heater or storage hot water heater or storage tank 250.

Effluent 200 enters a heat exchanger 220 where the effluent is cooled and cleaned resulting in a cleaned effluent stream 205. The FIG. 2b embodiment may be controlled so that coolant is pumped only when there is sufficient heat available to raise the water temperature. Heat may be conveyed to a heat exchanger in a hot water tank or to a fresh water inlet line so that the tank is filled as heat is added. In the latter case, a predictive controller may optimize for the preheating of water by postponing the addition of water to the tank until heat is available from the flue gas 200, since the waste heat load may be highly variable. In an embodiment, the hot water heater may an instant hot water type water heater (also known as a tankless water heater). In that case, the device 250 may simply be an inline insulated storage tank that stores water (and pre-heat) temporarily, providing as much pre-heat as available. In the latter case, water would be stored. Note that spray wash-cleaning of the cooled heat exchanger may be provided as in other embodiments discussed herein. Note that instead of the intermediate heat exchanger 240, a single double-wall heat exchanger may be provided to exchange heat between fresh water and the flue gas in the component indicated at 220.

Figure 2C:
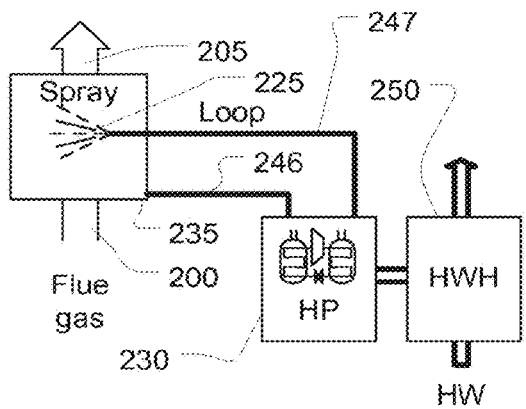
FIG. 2c illustrates a spray system, similar to that of FIG. 2a, using a heat pump in combination with a spray-type exhaust cooling device, rather than a liquid-air heat exchanger.
Figure 2D:
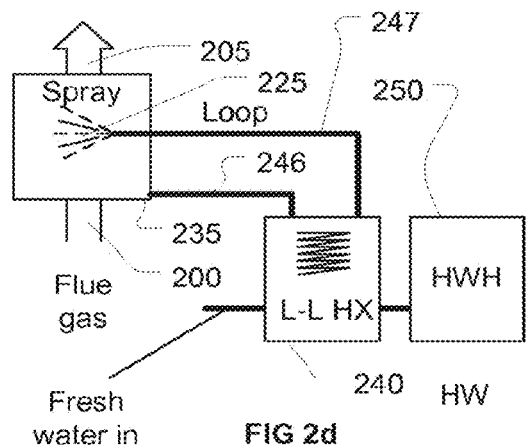
FIG. 2d illustrates a spray system, similar to that of FIG. 2b, using a water pre-heating heat exchanger in combination with a spray-type exhaust cooling device, rather than a liquid-air heat exchanger.

FIG. 2c illustrates a spray system, similar to that of FIG. 2a, using a heat pump in combination with a spray-type exhaust cooling device, rather than a liquid-air heat exchanger. FIG. 2d illustrates a spray system, similar to that of FIG. 2b, using a water pre-heating heat exchanger in combination with a spray-type exhaust cooling device, rather than a liquid-air heat exchanger. Runoff from the spray chambers 235 is recirculated back to the heat exchanger 240 to be cooled again. As in other embodiments, surfactant may be periodically added to the spray to wash the interior of the chamber. Outgoing 247 and return 246 lines are provided in both the FIGS. 2c and 2d embodiments. In other respects, these two embodiments are the same as described with reference to FIGS. 2a and 2b, respectively.

Figure 1G:
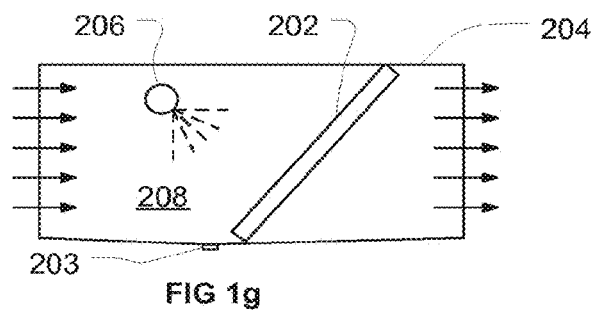
FIG. 1g illustrates a spray cooling heat exchanger employing a filter element.

Referring to FIG. 1g, in an alternative embodiment, a spray type cleaner and/or heat exchanger 204 is used in conjunction with a filter 202, such as a metal mesh or screen filter of the type commonly used as a prefilter in air conditioning systems. Such filters are known and made in various ways, for example, by multiple layers of perforated sheet metal forming tortuous passages. Water (or water plus surfactant) is sprayed by one or more nozzles 206 in a chamber 208 housing the filter and effluent flows through the filter 202. Water may be recovered and recirculated after transferring heat to a liquid heat exchanger (not shown) or disposed of if the application is only for cleaning.

The chamber 208 defines a collection area for collecting the liquid sprayed into the chamber 208." The collected liquid may be conveyed back to the nozzle 206 or disposed of, in alternative embodiments. In a preferred embodiment, the collected liquid is passed through a heat exchanger to recover heat transferred to the liquid from the flue gas. Also, or alternatively, in a preferred embodiment, the spray type cleaner and/or heat exchanger 204 of FIG. 1g is employed in a short-circuit exhaust system in which flue gas is cleansed by the spray type cleaner and/or heat exchanger 204 and conveyed back into the occupied space as shown in the embodiments below.

Figure 2E:
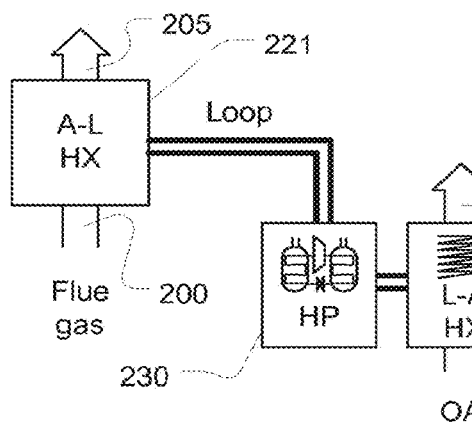
FIG. 2e illustrates a self-cleaning heat exchanger system.

FIG. 2e illustrates a self cleaning heat exchanger system. In this embodiment, the grease-laden effluent 200 enters a heat exchanger 221 where the effluent may be cooled and cleaned to produce a processed effluent stream 205. A cooling loop, including a heat exchanger 221, is cooled by a heat pump 230. The cooling loop chills the heat transfer surfaces of the heat exchanger 221. The heat pump 230 may be configured to drive the temperature of the heat exchanger 221 heat transfer surfaces to the point of freezing water.

Figure 2F:
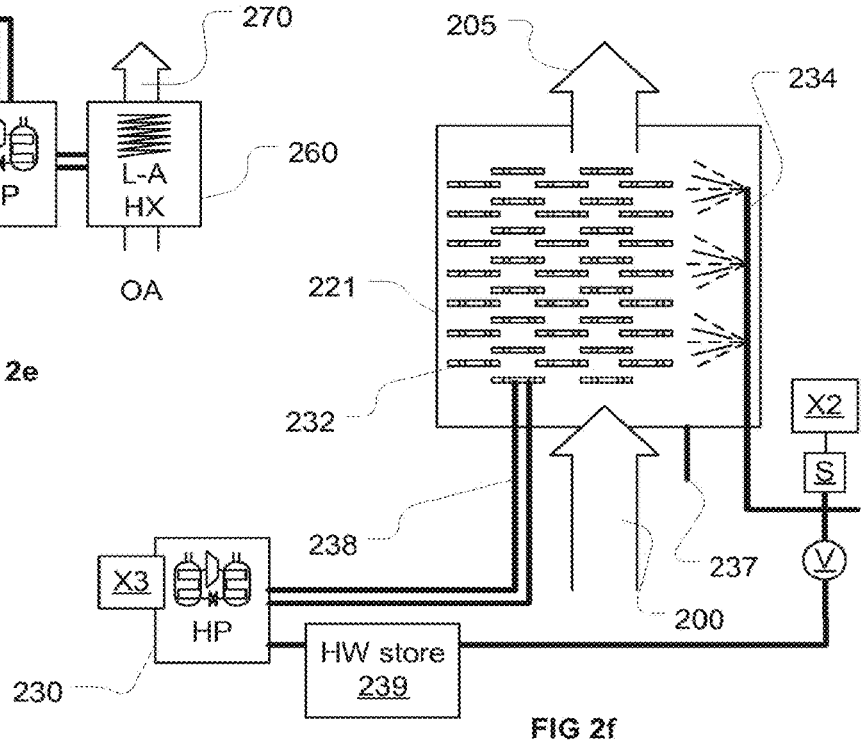
FIG. 2f illustrates a self-cleaning heat exchanger and heat recovery system.

Referring now also to FIG. 2f, the heat transfer surfaces 232 (typ.) of the heat exchanger 221 may be configured to freeze water on them, as do automatic ice makers. During low or no load cycles, the spray 234 may spray water on the heat exchange surfaces 232 to form layers of ice thereon. The ice surface can be used to cool the effluent stream and condense gaseous organics as well as act as a surface for attracting aerosol grease.

If the cold surface of the heat transfer surfaces 232 is maintained at a cold enough temperature, the water can remain frozen even while the hot exhaust fumes pass through the heat exchanger 221, though this is not essential. The purpose of the ice is to act as a shield to protect against grease accumulating on the heat transfer surfaces 232. The ice can be melted and regenerated during zero or low load portions of a cooking process cycle. The melting process can be augmented by reversing the heat pump 230. In addition, the during the ice-melting cycle, a controller X2 may add surfactant S to the water spray to help wash out grease that adheres to the heat exchange surfaces 232.

The heat pump 230 may be controlled by a controller X3 to heat the heat transfer surfaces 232 to a high enough temperature to melt all the ice. Then the washing spray can be applied and drained through drain 237. The heat pump 230 can be further controlled to continue to heat the surfaces 232 to a point where any solidified grease melts from the surfaces.

In an alternative embodiment, the heat pump 230 can reject heat to a temporary hot or warm water store that preheat tap water and stores it in a storage container 239. Controller X2 may selectively control a control valve V to add the warmed water for melting the ice, solidified grease, and for washing the heat transfer surfaces. In this case, the heat pump may or may not need to operate in a reverse mode.

One drawback of this system is that the air to liquid heat exchanger 220 will require periodic cleaning to remove any accumulated grease which builds up on the surface. An advantage of this system is that the heat pump 230 may run in a reverse cycle which may provide heating to the heat exchanger 221 which may melt and drain off any accumulated grease present.

Figure 3A:
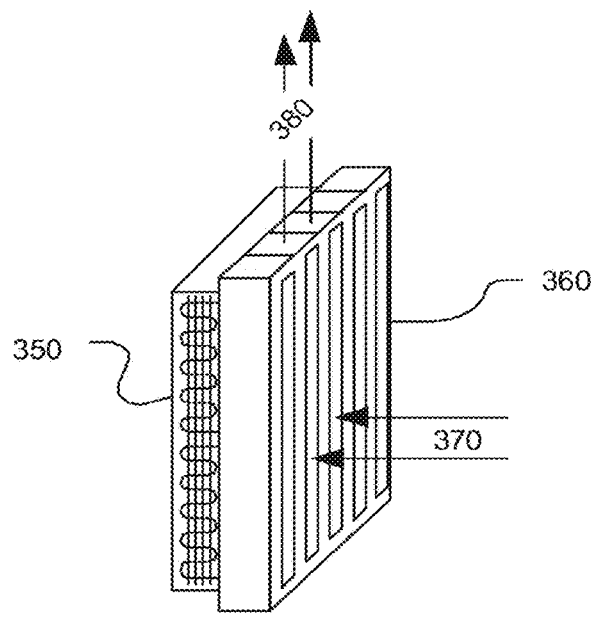
FIG. 3a illustrates a heat exchanger that is integrated with a grease extractor.

FIG. 3a illustrates a heat exchanger 350 that is integrated with a grease extractor 360 to both cool the effluent stream and improve the grease extraction performance of the extractor. The design of the grease extraction portion 360 may follow designs disclosed in U.S. Pat. No. 4,872,892 (Vartiainen, et al.) which is hereby incorporated by reference as fully set forth in its entirety herein. In the filter portion 360 the grease laden effluent stream from the cooking process enters the grease extractor 360 as shown by arrows 370. The effluent is cooled upon contact with the filter surfaces. In addition, grease aerosols that solidify on the surface may tendency to be re-entrained.

Cooler and cleaner air 380 may exit the grease extractor 360 through its ends. The heat exchanger 350 may be positioned against the back of the grease extractor 360 which may provide a cooler surface temperature. The cooling source for the heat exchanger 350 may be a liquid line which may utilize water, a phase change refrigerant, or another coolant fluid. An exemplary operating temperature is in the range of 33 to 36 degrees Fahrenheit range, which will condense grease and water vapor, but not freeze water.

Figure 3C:
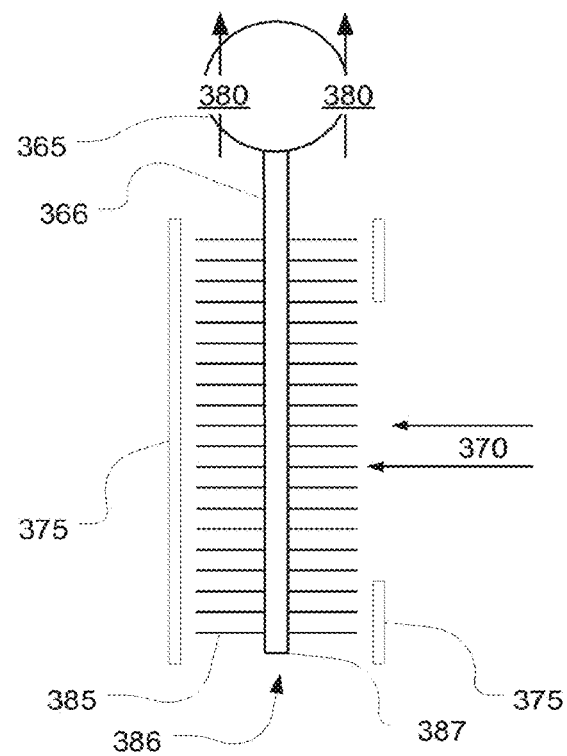
FIG. 3c illustrates a grease extractor that uses spine fins to enhance the grease extraction performance of the extractor.
Figure 3B:
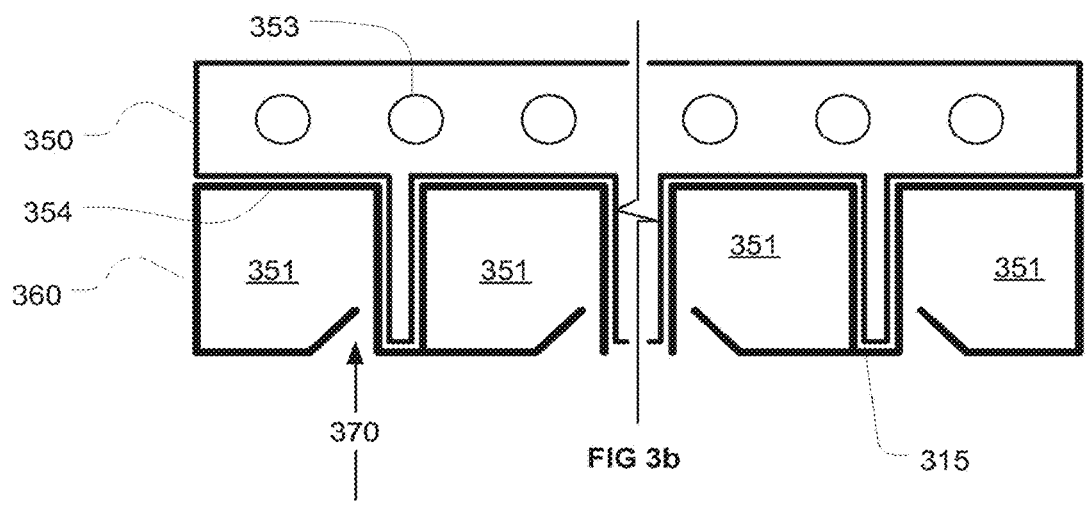

FIG. 3b illustrates a top view of the heat exchanger and grease extraction filter combination of FIG. 3a. Grease laden effluent 370 from the cooking process enters the grease extractor 320 as indicated by arrows 370. Channels for the heat transfer fluid 353 conduct heat from fins 315 and the back surfaces 354 of the vortex chambers 351. The effluent cools upon contact with the filter surfaces within vortex chambers 351.

FIG. 3c illustrates a grease extractor that uses spine fins 385 to enhance the grease extraction performance of the extractor 360. In this embodiment a filter 375 generally configured as filter the one previously indicated at 360 (FIG. 3a) has a spine-finned heat exchanger 386 with a heat pipe 387 conveying heat to a header 365 that conveys coolant. Effluent 370 enters the filter 375 and collects on the filter walls and the fins. The cleansed effluent 380 leaves the filter 375 in the same manner as the filter embodiment of FIGS. 3a and 3b. The spine-finned heat exchangers 386 may be removed periodically for cleaning.

Referring now to FIG. 3d, an embodiment of a finned-tube heat exchanger 395 integrated with a vortex-type grease filter 380 is shown. The fins are illustrated as cylindrical volumes, indicated at 382, which show the space occupied by the fins collectively. Collectively, the fins form a brushlike heat transfer inserts 392 and are connected to convey heat to/from a centrally located heat pipe 388 which runs into a header tube 384. The heat pipe may adopt a serpentine shape as indicated at 386 or have another type of heat transfer augmentation such as fins to transfer heat to a fluid medium carried by the header tube 384. As illustrated, each heat pip 388 is connected to two heat transfer inserts, but other configurations are possible as will be apparent to those skilled in the art. A quick-connector 393 and 394 may be provided to connect a pipe or another header tube indicated at 390.

To assemble, the heat transfer inserts 392 are slid into the vortex chamber exits 396. To disassemble, the heat transfer inserts 392 are extracted from the vortex chamber exits 396. The vortex-type grease filters 380 can be removed with the heat transfer inserts 392 in place. Since the heat transfer medium that flows through the header tube 384 may be a low pressure circuit (and even if not) the connectors 392 and 394 may be pressure fit connectors. In addition, the entire heat exchanger 395 unit may be made as a multiple-use disposable unit.

Referring now to FIGS. 3e and 3f, a combination heat exchanger and grease filter 440 has zigzag shaped fins 444 which force effluent running across the fins through a tortuous path when the effluent stream is appropriately conveyed through the filter 440, as shown in FIG. 3f. A heat transfer fluid is distributed and recovered through headers 441 and 442. Multiple heat transfer tubes 446 connect the headers 441 and 442 and receive heat energy by conduction through the fins 444. The filter 440 can be arranged in a ducting component or system, at least a portion of which is shown at 456, such that effluent traverses the fins and liquid precipitate 452 is collected from the ducting 456. In a particular embodiment, spray nozzles 448 spray water, or water plus a surfactant, onto the fins 444. The spray liquid may be recovered and used as a heat transfer fluid, recirculated or partially recirculated. The orientation of the filter 440 and the particular shapes of the fins 444 can be such that grease 452 can flow to a collection area. For example, the shape of the fins 444 can define troughs through which the grease runs and the housing 446 can further define collection paths for the grease.

Figure 4A:
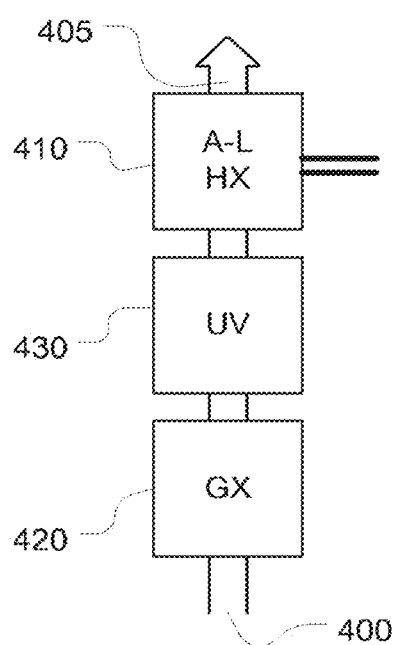
FIG. 4a illustrates the use of ultraviolet light or other ozone generating devices which may be used to cleanse fume-laden air and gases upstream of a heat exchanger.

FIG. 4a illustrates the use of ultraviolet light or other ozone generating devices which may be used to cleanse fume-laden air and gases upstream of a heat exchanger. The embodiments shown in FIGS. 4a to 4d include mechanisms for cleaning the heat exchanger or reducing the quantity of fouling products from reaching the heat exchanger surfaces. In these embodiments, grease laden exhaust stream 400 first passes through a grease extraction filter 420 whereby larger particulates are removed from the air stream.

After the exhaust stream exits the primary grease extractor 420, it is exposed to UV light 430. The UV light 430 is preferably directed toward the surface of the heat exchanger 410 which may help to prevent grease from accumulating on the heat exchanger surface. Ultraviolet lamps may be available in two broad categories: ozone producing and non-ozone producing. Ozone producing lamps may provide the benefit of oxidizing the grease into other compounds by reacting with grease molecules in the exhaust air 400. One drawback of utilizing ozone producing lamps is that the ozone may need to be removed. Methods which may be used for removal of ozone are described later in this document.

Figure 4B:
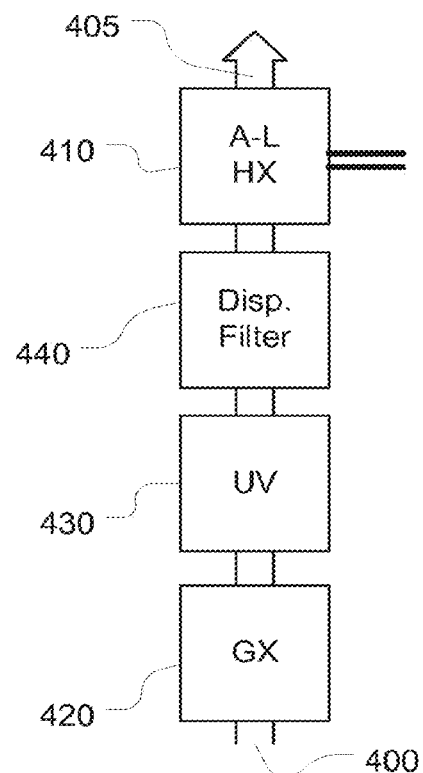
FIG. 4b illustrates the use of ultraviolet light to help keep a heat exchanger clean.

FIG. 4b illustrates the use of ultraviolet light to help keep a heat exchanger clean. when used with a grease extractor over cooking appliances such as a stove, fryer or grill. FIG. 4b is similar to the previous embodiment but adds a disposable filter 440 into the system. In this embodiment the disposable filter 440 may be used as a means of extracting grease prior to the grease reaching the heat exchanger 410. UV light 430 may be used in this embodiment to maybe keep the disposable filter 440 clean, whereby it's useful life may be extended and in practice it may not have to be replaced as often as a system which may not use ultraviolet light 430.

Figure 4C:
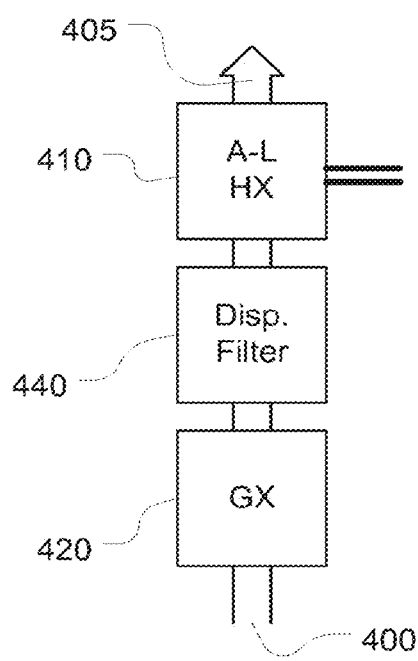
FIG. 4c illustrates the use of a disposable filter which may keep a heat exchanger clean when used with a grease extractor over cooking appliances such as a stove, fryer or grill.

FIG. 4c illustrates the use of a disposable filter which may keep a heat exchanger clean when used with a grease extractor over cooking appliances such as a stove, fryer or grill. In this embodiment the grease laden air 400 from a cooking process enters the primary grease extractor 420, at which point significant amounts of grease particulate may be removed from the air stream. Additionally, if the grease extractor is at a sufficiently cool temperature, some of the grease vapor may condense out on the grease extractor 340 surfaces. After the air exists the grease extractor 420 it may be further cleaned by a disposable filter 440. The filter may be manufactured from paper, plastics, or other materials. The disposable filter 440 may furthermore be of the HEPA variety (which has a particulate removal efficiency of 99.97% at 0.3 micron particle size) or ULPA filter variety (classified as removing 99.999% of 0.1 to 0.2 micron particulates). The results is that a much cleaner air stream meets the air to liquid heat exchanger 410 which may results in better heat transfer performance and may cool the entering air. The air stream 405 leaving the system may be cleaner and cooler than the entering air stream 400. One advantage of this system is maintenance and cleaning costs may be reduced through the use of a disposable filter 440 due to reduced labor expenses.

Figure 4D:
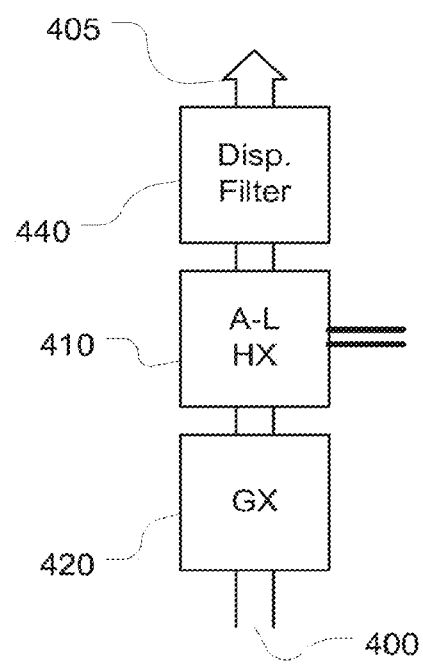
FIG. 4d illustrates the use of a disposable filter which when used at the outlet of an exhaust system may reduce ambient emissions when used with a grease extractor over cooking appliances such as a stove, fryer or grill.

FIG. 4d illustrates the use of a disposable filter which when used at the outlet of an exhaust system may reduce ambient emissions when used with a grease extractor over cooking appliances such as a stove, fryer or grill. This embodiment has similar performance to the previous embodiment but may be used to reduce ambient emissions further after the grease extractor 420 and the heat exchanger 420 provide an initial degree of purification. In this embodiment the grease laden air 400 enters the system, passes through a primary grease extractor 420 which may remove particulate matter from the air stream. The air may then be cooled by contact with a heat exchanger 410 which may further reduce the amount of grease remaining in the air stream. Finally the air stream enters a disposable filter 440 which may be manufactured form paper, plastics, or other materials. The air which is exhausted from the system 405 may be cleaner and cooler than the air which enters the system 400.

Note that in the embodiments of FIGS. 4a to 4d, the heat exchanger components 410 can also represent any of the heat exchanger embodiments discussed in the instant specification.

Figure 5A:
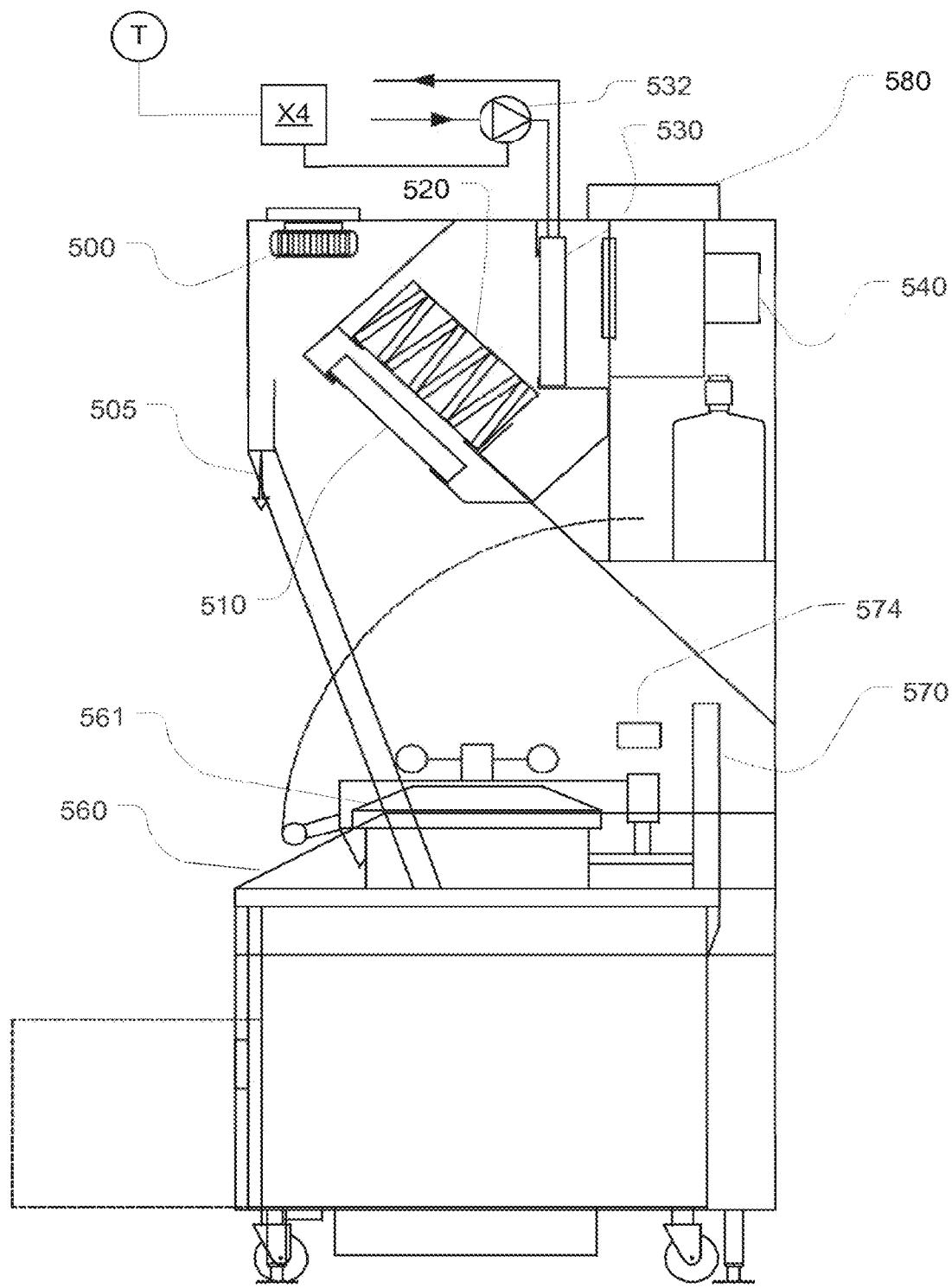
FIG. 5a illustrates a non-vented hood which may utilize front air jets 505 to enhance the capture performance.

FIG. 5a illustrates a non-vented hood which may utilize front air jets 505 to enhance the capture performance. See U.S. Pat. No. 6,851,421, hereby incorporated by reference as if set forth in its entirety herein for hood design variations and details. In this embodiment, an internal fan 500 may be used to produce a vertically oriented jet 505 which may form an air curtain at the front plane of the hood causing emissions produced by cooking appliances to remain inside the hood reservoir area. In one notable embodiment, fumes from a pressure fryer 560 are treated by the hood. Emissions may be released from the top of the appliance when it opened and from a vent 570 located at the rear of the appliance when it is cooking.

When emissions are released they travel to the primary grease extractor 510 and they may then go through a secondary grease extractor 520. The exhaust air stream may then go into a charcoal type of filter 520 which may reduce the amount of odor emitted to the ambient space and then through an exhaust fan 540 terminating in an exhaust collar arrangement 580. A heat exchanger 530 may be provided to cool the exhaust. The advantage of a non-venting hood is that no external ductwork is required to ventilate the cooking products to outdoors. A fan 540 draws fumes and exhausts treated fumes from an outlet 580.

A controller X4 may control cooling flow to the heat exchanger in response to the ambient temperature. During period of positive space conditioning heat load, it may be desirable to recover heat from the exhaust, so the controller X4 may operate as a thermostat, controlling a pump 532 to determine if the heat exchanger 530 is operative to remove heat. The controller X4 may control the other types of heat exchangers and cooling devices discussed herein.

Figures 5B, 5C:
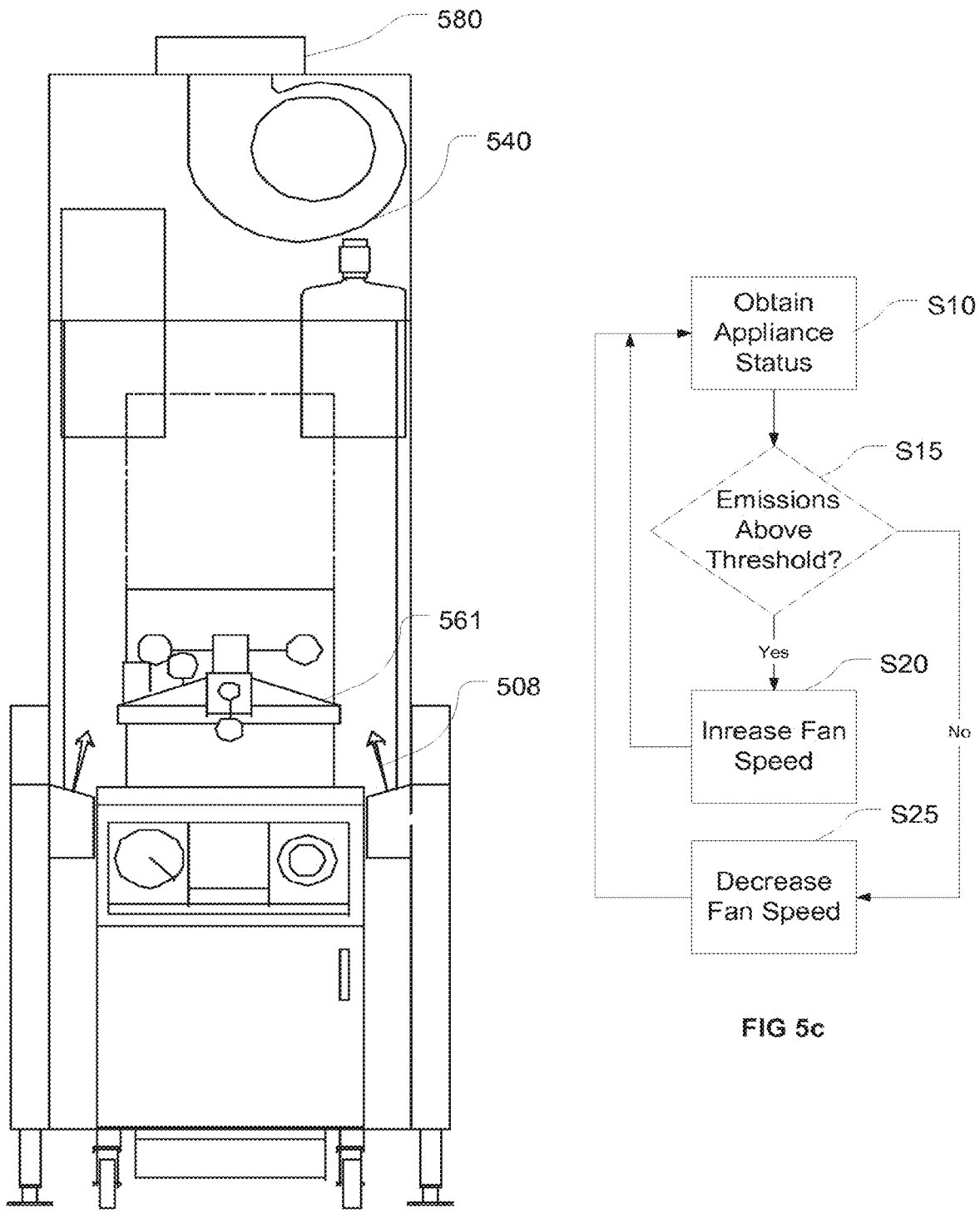

The fryer 560 has a pressure cover 561 which is periodically closed when a batch of food is to be cooked. The load profile consists of a pulse when the cover 561 is opened after a batch is cooked, a smoothly varying load during cooking which tends to taper toward the end of a cooking cycle, and an idle load during which the fryer is open and not cooking. The cooker may be fitted with an interlock 574 to detect the stage of the cooking cycle based on the cookers configuration. A controller (not separately shown) may be configured to use a status signal from the interlock as well as an internal clock to determine the point in the cooking cycle and to predict upcoming filtering requirements and control the purifying systems accordingly. For example, as discussed with reference to the embodiment of FIGS. 2*e* and 2*f*, the clearing and formation of ice may be done during low load periods in response to the controller responsively to the cooker status signal. For example the cooker status signal may indicate the position of the pressure cooker cover 561, the cover lock, the oil temperature, the fuel consumption rate, a primary controller for the cooker (e.g., start batch, keep hot, idle, etc.). FIG. 5*b* is a front-on view of the embodiment of FIG. 5*a*. From this perspective, side jets 508 that are directed upwardly into the hood, are visible.

FIG. 5*c* illustrates a control algorithm which may be used to vary the exhaust airflow rate of the non-ventilating hood which may improve the grease removal performance of the system when used over cooking appliances such as a stove, fryer, or grill. In step S10, the appliance status is determined. The appliance status may include total load (which may be a predicted parameter based on fuel consumption rate, exhaust fume temperature, incipient breach—See U.S. patent Ser. No. 10/907,300 filed Mar. 28, 2005, hereby incorporated by reference as if fully set forth herein—or any other load predictor or indicator) In step S15, the controller determines if the exhaust rate needs to be increased or can be decreased and in steps S20 and S25, the corresponding control, in this case fan speed, is activated. According to this control algorithm, a signal from the appliance may be used to determine whether the appliance is cooking food (which may be synchronous with producing grease) or in a non-cooking state. If the status of the appliance is determined to be cooking, the fan speed may be increased to capture the effluent which may be produced over cooking appliances, such as a stove, fryer, or grill.

Advantages of this control algorithm may include energy savings due since the fan may run at a lower operating speed during idle conditions. An additional advantage is that the grease extraction removal efficiency may increase at higher airflows which may correlate to when the highest grease emissions are released by the appliance.

Figure 6A:
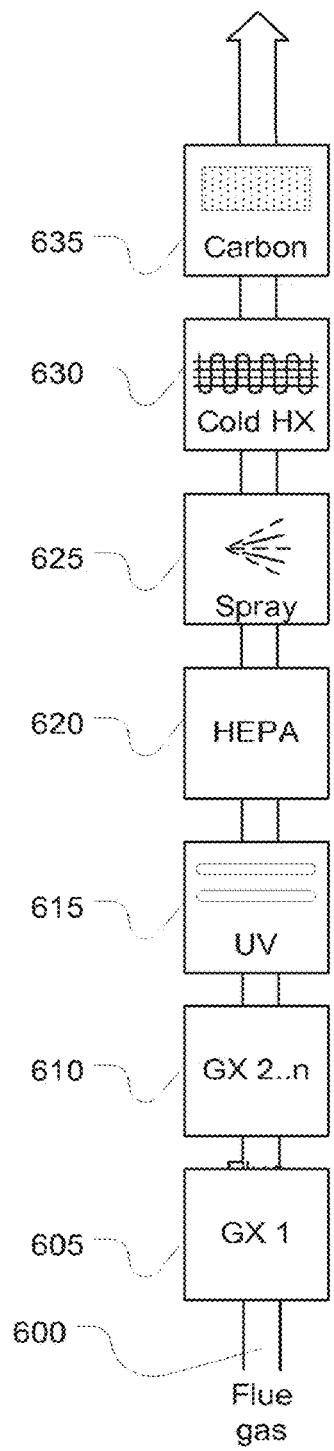
FIG. 6a illustrates means of providing multiple stages of grease extraction which may provide for enhanced removal of the effluents produced over cooking appliances such as a stove, fryer or grill.

FIG. 6*a* illustrates means of providing multiple stages of grease extraction which may provide for enhanced removal of the effluents produced over cooking appliances such as a stove, fryer or grill. In this embodiment the grease laden air 600 from a cooking process enters the primary grease extractor 605, at which point significant amounts of grease particulate may be removed from the air stream. The grease laden air 600 may enter a series of secondary grease extraction filters 610 which may vary in number from one to many filter stages. These secondary filters 610 may remove more of the grease particulate from the exhaust air stream and may or may not be present in practice. The exhaust air may enters an ultraviolet light chamber 615 wherein the grease may chemically react with both the ultraviolet light and ozone which may be generated by the ultraviolet lamps. The grease laden air 600 may enter a filtration stage of HEPA classified filters 620 which may remove fine particulate from the exhaust airstream. This stage of filtration may also be manufactured from a higher efficiency particulate removal material such as ULPA classified filters. The grease laden air 600 may enter a spray chamber 625 where a spray nozzle (not shown) may spray a cool liquid with may result in grease particulate and vapor being washed or condensed out of the air stream. One disadvantage of a spray system may be that it requires detergent or other additives to be added which may remove grease buildup in the spray chamber 625. The grease laden air 600 may be diverted through or around a cold heat exchanger 630 which may condense out grease particulate and vapor if it is cooler than the dew-point temperature of the grease laden air 600. The grease laden air 600 may pass through a carbon based filter 635 which may be of the charcoal variety which may reduce the level of odors emitted to the ambient space.

Furthermore, the embodiments shown may be used singularly or in any combination and order to achieve the optimal grease removal affect for a given cooking appliance operation. The air exiting the system may be cleaner, cooler, and drier than the entering grease laden air 600.

Figure 6B:
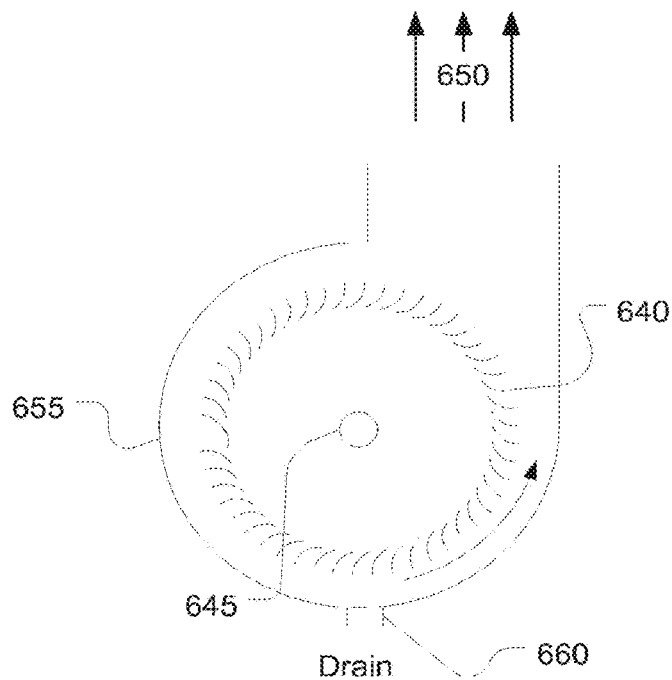
FIG. 6b illustrates an exhaust fan employed as a grease removal and collection device for enhanced removal of the effluents produced over cooking appliances such as a stove, fryer or grill.

FIG. 6*b* illustrates an exhaust fan employed as a grease removal and collection device for enhanced removal of the effluents produced over cooking appliances such as a stove, fryer or grill. The grease laden air (not shown in this view) enters the fan cage 640 laterally. As the fan motor (not shown) rotates the fan cage 640, grease may be slung tangentially from the cage 640 impacting the side of the fan shroud 655. Any grease which accumulates inside the fan shroud may run down to the grease drain 660 where it may be collected. The air exiting the system 650 may be cleaner than the entering grease laden air.

Figure 6C:
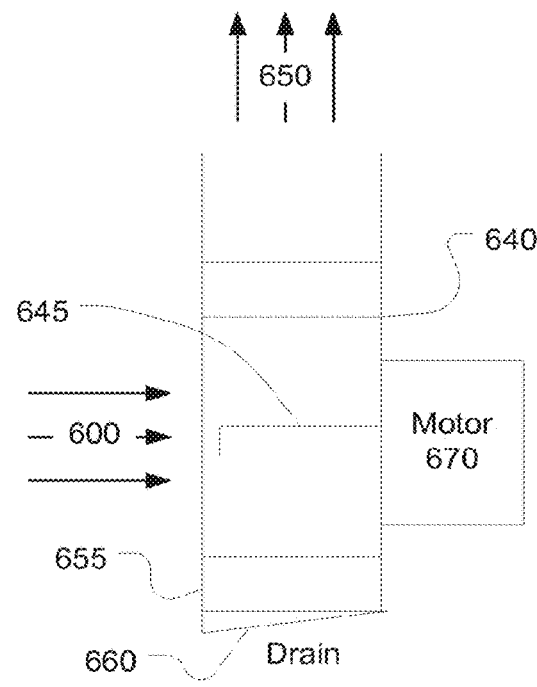
FIG. 6c illustrates the side view of an exhaust fan used as a grease removal and collection device for enhanced removal of the effluents produced over cooking appliances such as a stove, fryer or grill.

FIG. 6*c* illustrates the side view of an exhaust fan used as a grease removal and collection device for enhanced removal of the effluents produced over cooking appliances such as a stove, fryer or grill. The grease laden air 600 enters the fan cage 640. As the fan motor 670 rotates the fan cage around a shaft 645, the grease may be slung out from the fan cage impacting on the fan shroud walls 655. The grease may run to the bottom of the fan housing and be collected in a grease drain 600 which may be sloped to facilitate grease runoff. The air exiting the system 650 may be cleaner than the entering grease laden air 600.

Figure 7A:
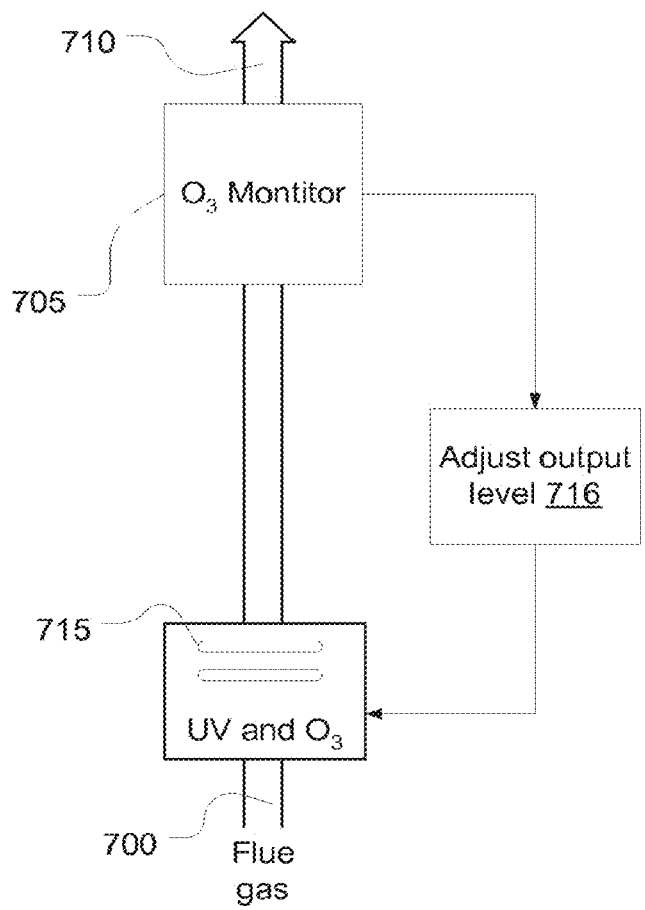
FIG. 7a illustrates a feedback control system for maintaining a set level of ozone production from ultraviolet lamps when used over a cooking appliance such as a stove, fryer, or grill.

FIG. 7*a* illustrates a feedback control system for maintaining a set level of ozone production from ultraviolet lamps when used over a cooking appliance such as a stove, fryer, or grill. In this embodiment fumes 700 enter a chamber containing ultraviolet lamps 715. If the lamps produce ozone a control system to maintain a threshold level of ozone emissions may be desirable. In this control algorithm, an ozone monitor 705 may be used to detect the level of ozone present in the air stream 700. The ozone level is modulated by a controller 716 to maintain a detectable but low level of ozone in the exhaust stream. The system is preferably configured to maintain a maximum predetermined level of ozone to ambient conditions.

Figure 7B:
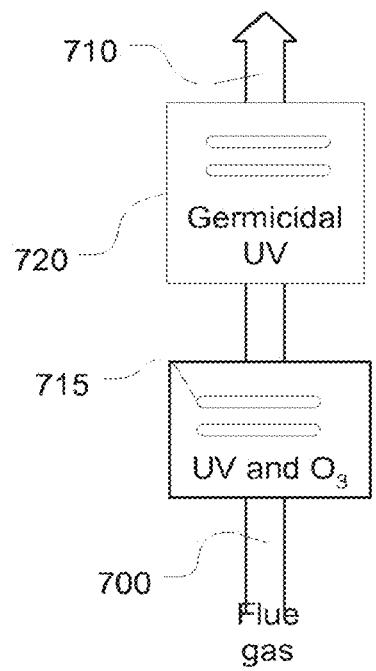
FIG. 7b illustrates the use of germicidal ultraviolet lamps which may destroy ozone generated previously from sources such as ultraviolet, ozone producing lamps when used over cooking appliances such as a stove, fryer, or grill.

FIG. 7*b* illustrates the use of germicidal ultraviolet lamps which may destroy ozone generated previously from sources such as ultraviolet, ozone producing lamps when used over cooking appliances such as a stove, fryer, or grill. In this embodiment the grease laden air 700 is exposed to ultraviolet, ozone producing lamps 715 which may react with the grease and may oxidize some of it. It may be undesirable to emit excess ozone to the atmosphere or to an indoor space. To alleviate excess ozone, germicidal ultraviolet lamps of the kind which do not produce ozone may be housed in a chamber 720 and used to destroy the excess ozone. The exiting air stream 710 may have little or no ozone present.

Figure 7C:
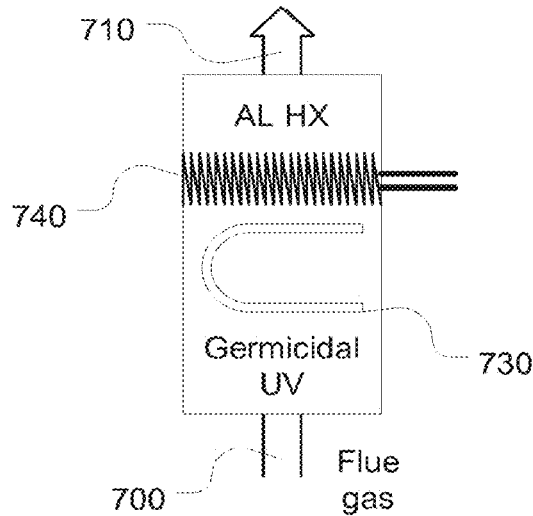
FIG. 7c illustrates a means of cleaning a heat exchanger which may get coated with grease when exposed to the effluents produced over cooking appliances such as a stove, fryer or grill.

FIG. 7*c* illustrates a means of cleaning a heat exchanger which may get coated with grease when exposed to the effluents produced over cooking appliances such as a stove, fryer or grill. In this embodiment grease laden air 700, which may be of the type produced by cooking appliances, may coat a heat exchanger 740 when present in the exhaust air stream. Germicidal lamps may be used to destroy any grease which may accumulate on the surface of the heat exchanger 740. One advantage of this system is that germicidal ultraviolet lamps are available in models that do not produce any ozone emissions, which means that ozone abatement is not needed with this type lamp.

Figure 7D:
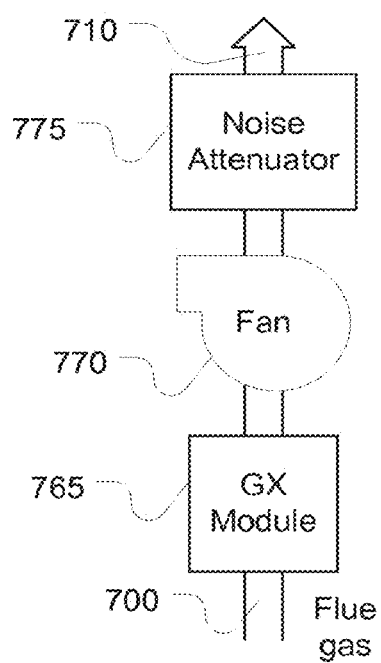
FIG. 7d illustrates a noise attenuator which may also be used as a grease removal device when present in a system used over a cooking appliance such as a stove, fryer or grill.

FIG. 7*d* illustrates a noise attenuator which may also be used as a grease removal device when present in a system used over a cooking appliance such as a stove, fryer or grill. In this embodiment the grease laden air 700 passes through a grease extractor 765 which may remove different amounts of particulate matter. An exhaust fan 770 may be used to exhaust the air. A noise attenuator 775 may be placed after the exhaust fan 770 to reduce the noise levels present in the ambient space. The noise attenuator 775 furthermore may be used as a final stage of filtration to remove additional levels of grease from the air stream. If the area of the noise attenuator 775 were larger than the outlet of the exhaust fan 770, noise may be further reduced due to a reduction in velocity through the noise attenuator 775 relative to the exhaust fan 770 used alone.

Figures 8D, 8E:
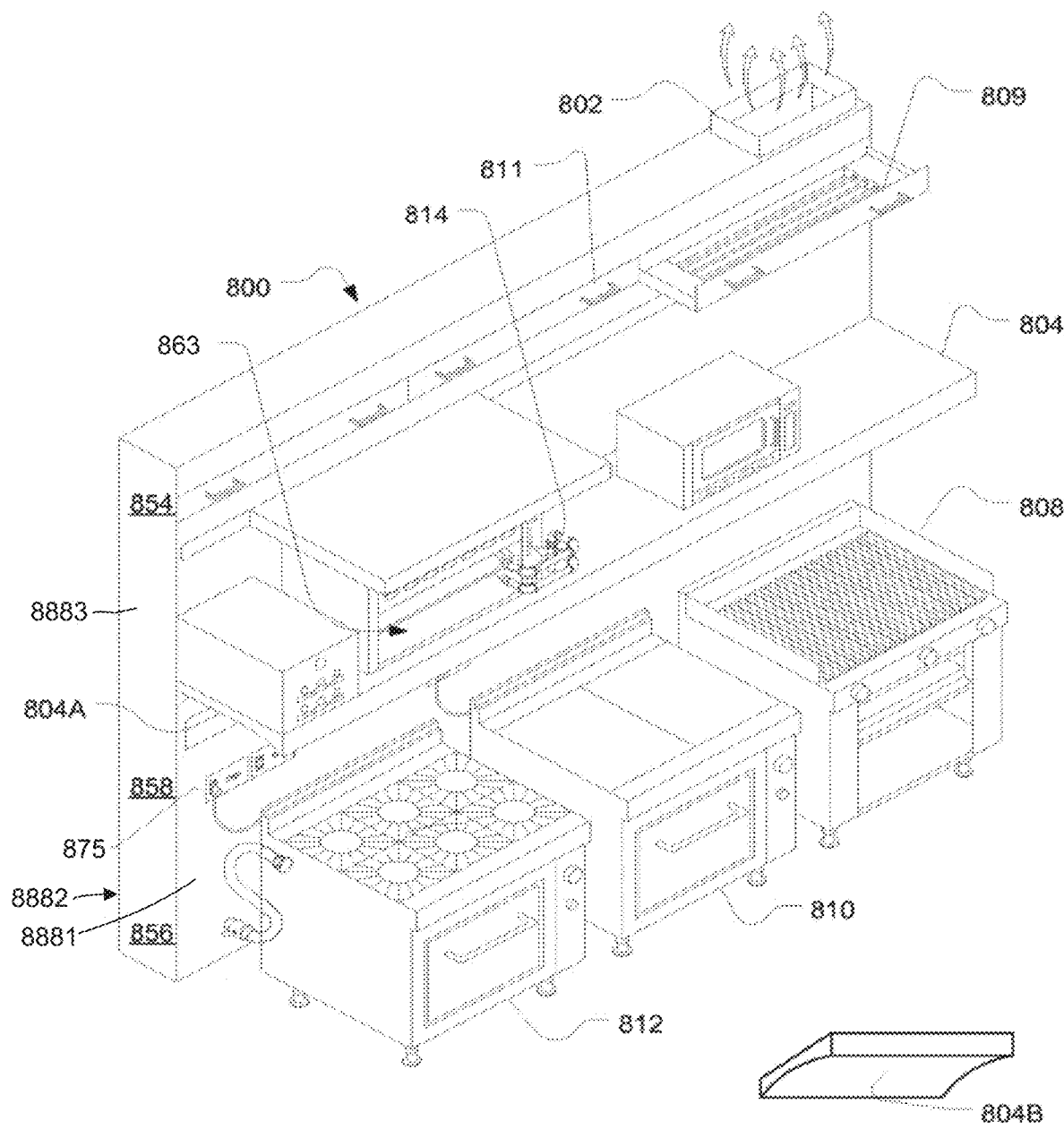

Referring to FIGS. 8*a* and 8*c*, a modular wall unit 801 houses duct section 854, an electrical section 858, and a plumbing section 856. As shown in the figures, the duct section 854 is stacked on top of the electrical section 858, which is stacked on the electrical section 856, forming a stack. Each of these sections 854, 856, and 858 has a front wall and an opposed rear wall. When the sections 854, 856, and 858 are stacked as shown in FIGS. 8*a*-*d*, the front walls together form a pair of substantially planar surfaces 8881 and 8882 of the modular wall unit 801. As shown in FIGS. 8*a*, 8*b*, and 8*d*, the planar surface 8881 is spaced apart from the planar surface 8882 by a predetermined distance, thus creating interior wall region 8883 inside of the modular wall unit 801, with portions of the interior wall region 8883 being in each of the sections 854, 856, and 858. The duct section 854 may constitute a continuous plenum that runs between adjacent modular wall units 801. A filter module 867 holds a grease filter cartridge 852 and slides in and out on glides one of which is indicated at 850. The filter module 867 allows the filter cartridge 852 to be removed for cleaning. A suction applied to the duct section 854 interior plenum via exhaust collar 866 draw fumes through the filter and through an aperture 853 in the top of the filter module 867. The filter module 867 also includes a small plenum section 864 that connects to a mini-hood 870 conduit 871 which transfers some of the suction into the filter cartridge 852 to the conduit 871 drawing air and fumes into an inlet 862. Air and fumes are drawn into the inlet 862 to isolate an appliance in the space indicated at 863 which may installed such that it rests on shelf 868. Shelf 868 may act as a truncated hood to help fumes pass into the filter inlet 869 from an appliance located below the shelf 86. See FIGS. 8*d*, 9*a*, and 9*b* for examples of appliances being protected in this way.

The electrical section 858 provides electrical services within the modular wall units 801 as well as connectors 840 to interconnect the service components in adjacent wall unit 801 electrical sections 858. Services may include branch wiring (not shown), electrical outlets 875 for appliances, and connectors 840 for adjacent wall units 801 or to service supply (not shown) to connect a series of interconnected wall units 801 to a primary supply.

In an analogous manner to the electrical sections 858, plumbing sections 856 provide interconnects, supply terminals for water supply and drainage, and connectors 841 to interconnect the plumbing (not shown) of adjacent wall units 801 and a series of interconnected wall units 801 to a primary supply and/or primary drain. Plumbing for fuel supply may also be provided, for example to supply gas appliances. Also contemplated are fire suppression water or liquids.

Note that plumbing 856 and electrical 858 sections can also supply electrical signals interconnection and terminals for sensors for control systems as well the distribution or drainage of fluids other than water and wastewater. For example, grease drainage may also be provided, surfactant or cleaning agent distribution may be provided for and/or fire suppression chemicals supply as well.

Referring now also to FIG. 8*b*, the types of filter modules 851 and 853 and the locations where they are installed may be varied to suit the particular mix of appliances to be covered. One type of filter module may be configured to cooperate with an appliance hood 892 that may be configured to be attachable to the modular wall 800 duct section 854. In FIG. 8*b*, the location of slides 855 for the filter modules 851 and 853 are located higher than the corresponding locations of FIG. 8*a*.

The embodiment of a filter module indicated at 851 has an adjustable damper panel 848 which can pivot up and down as indicated by arrow 846 to throttle flow through the filter module 851 thereby allowing multiple exhaust modules sharing a series of modular wall units 803 to be balanced. The damper panel 848 may, in an embodiment, be automated.

Note that dashed lines such as the typical one indicated at 877 illustrate how components can be attached to the modular wall unit 803. Also, the modular wall units 801, 803, may be configured with movable, removable, and/or replaceable panels 838*a*, 838*b*, and/or 838*c* to allow access to components such as electrical connections or to create openings for ducting.

Referring now to FIG. 8*d*, a perspective view of a modular wall 800 showing an arrangement of appliances and components that can be added is shown. In this embodiment, a range 812, an oven and/or fryer 810, and a grill 808 are under a shelf 804 that does double duty as a truncated hood, as described with reference to the shelf 868 in FIGS. 8*a* and 8*b*. As can be partly seen in FIG. 8*d* and better in FIG. 8*e*, the shelf 804 can have a smooth curved surface 804A, (804B in the short shelf embodiment of FIG. 8e) to help it function as a fume capture device and also to help make it easy to clean of grease films that may form on the surface.

The fumes are guided by the surface 804A, 804B to be drawn into the filter inlet 869 as discussed with reference to prior embodiments. The fumes flow through the hood section 854 and, the current embodiment, through an ultraviolet treatment section 811, a section of which is shown pulled out as a module which includes a service drawer 809. The suction required to draw the fumes is provided by a connection to an exhaust system (not shown) via an exhaust collar 802. FIG. 8d also shows electrical 802 and plumbing 814 terminals and connectors. Although not specifically shown, the modular wall 800 may consist of any number of horizontal segments that are connected together as illustrated and discussed with reference to FIG. 8c.

Figure 9A:
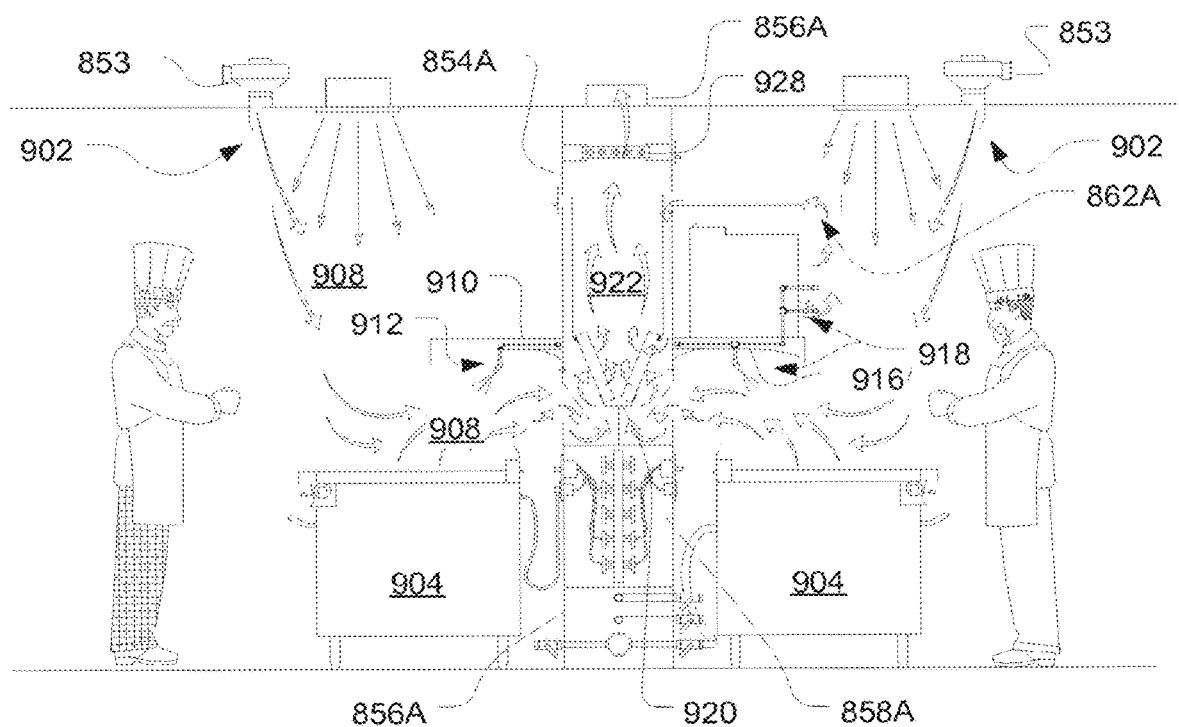
FIGS. 9a and 9b shows double sided and single-sided embodiments of the modular wall system of FIGS. 8a-8d, respectively, protecting appliances on both sides.
Figure 9B:
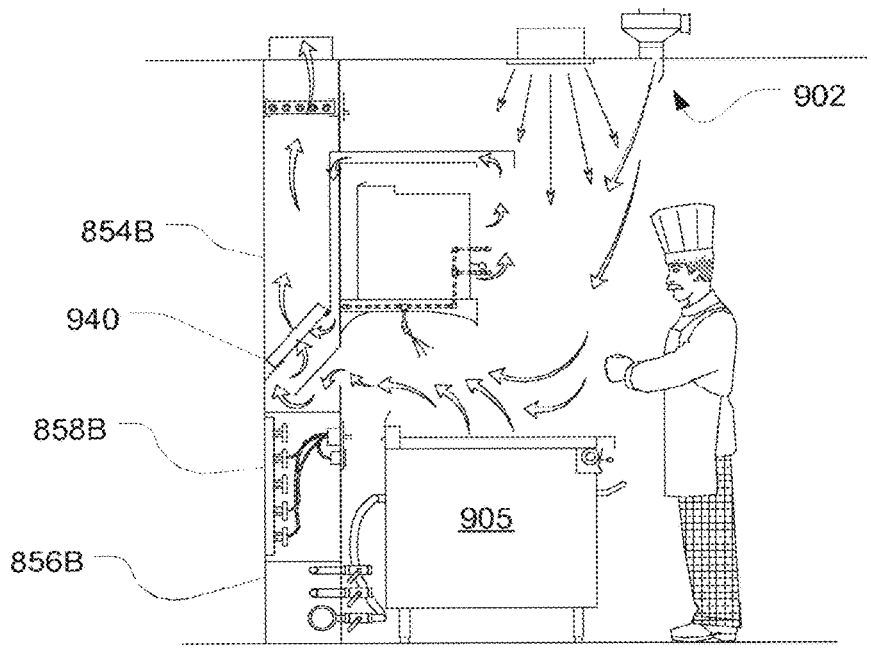

FIGS. 9a and 9b shows double sided and single-sided embodiments of the modular wall system of FIGS. 8a-8d, respectively, protecting appliances 904 on both sides. In FIG. 9a, it can be seen how fumes 908 can flow from both sides of a double modular wall into a common plenum 922 forming the interior of a double duct section 854A. Also visible in this figure is the ultraviolet light treatment module 928 and exhaust collar 856A. Note that the exhaust collar 856A may be provided in a subset (for example, one) of the adjacent modular wall units (shown side by side in FIG. 8c). Also visible in this figure is the intake for the mini-hood 862A, fire suppression terminals 912, 918 and the truncated hood 916. A double filter module 920 is also shown.

Ventilation air may be blown into the vicinity of a worker in front of the hood as shown by the jet at 902. In the embodiment, a rooftop fan 853 is shown immediately above, but this is a figurative representation and a concrete implementation would often involve ducting and connection or a common supply of make-up air. The ventilation air jet 902 is preferably of fresh filtered or outdoor air and is blown into a zone 908 that is in front of the appliance 904 to help create a clean breathable zone. Any fumes that escape from complete containment by the exhaust system tend to travel away from zone 908, which has the benefit of ensuring the air in the vicinity of the worker is not polluted. A shelf without a mini-hood 862 is shown at 910.

On the single sided modular wall, FIG. 9b, an appliance 905 on one side is protected. The elements of FIG. 9b are described elsewhere for the most part. The filter module 940 as in the embodiments has a single filter cartridge. The wall has duct, 854B, electrical 858B, and plumbing 856B sections.

Additional sections and terminals may provide services for wired data routing and sewage drainage. In an embodiment, the data routing, for example provided by cabling defining a bus, are included in the electrical section. Connections to sensors, appliances with integrated controls, sensors, and communications components, end effectors, and other controllers and/or embedded systems may be provided for in a manner similar to that discussed with reference to the electrical connections. For example, a standard type of terminal may be connectable to the data routing wiring.

In another embodiment, the data routing is provided for by low cost wiring integrated in every type of section. Sewage draining may be provided in its own type of module or combined with the plumbing module. Connections can be provided in ways that are essentially as described above with reference to plumbing connections.

Note that while the embodiments herein have described in which sections carrying electrical, gas, and plumbing, etc., it is possible to provide these services in a service distribution duct which encloses all type of distribution channels. Preferably, if exhaust flow volumes are large, exhaust would be provided outside such a distribution duct.

Also, although the embodiments of modular walls described above include a single type of exhaust network, in an embodiment, the modular walls provide separate exhaust networks for high and low temperature exhaust. For example, in an embodiment, the combustion fumes from a fuel fired fryer are carried by the high temperature exhaust network while the low temperature exhaust from a hood located above the fryer are carried by the low temperature network. By separating the high temperature exhaust network from the low temperature network, heat from the high temperature network can be extracted and used more efficiently than if the exhaust streams are mixed. For example, high temperature heat from the high temperature network may be used to pre-heat potable water or for direct conditioning of make-up air in winter. Heat from the low temperature network may be used as a heat source, or a part of a heat source, for a heat pump water heater, as described above.

Figure 9C:
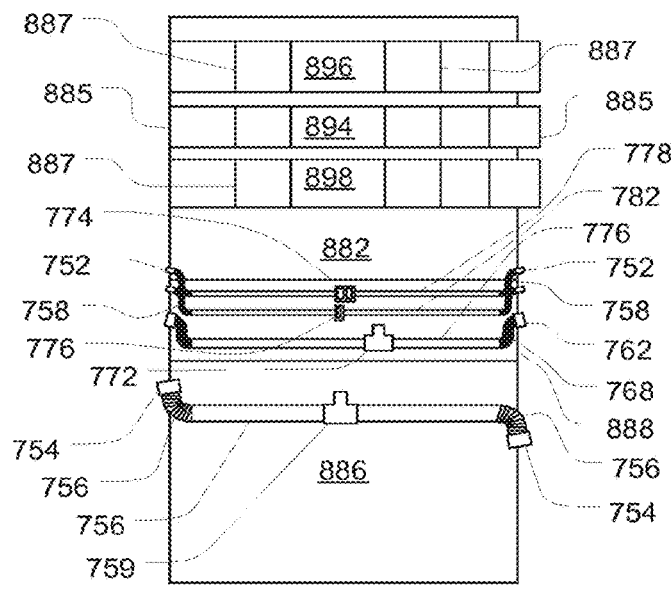
FIGS. 9c and 9d shows an embodiment of a set of modular wall modules showing features relating to interconnection, FIG. 9c showing internal structure and FIG. 9d showing external surface features.
Figure 9D:
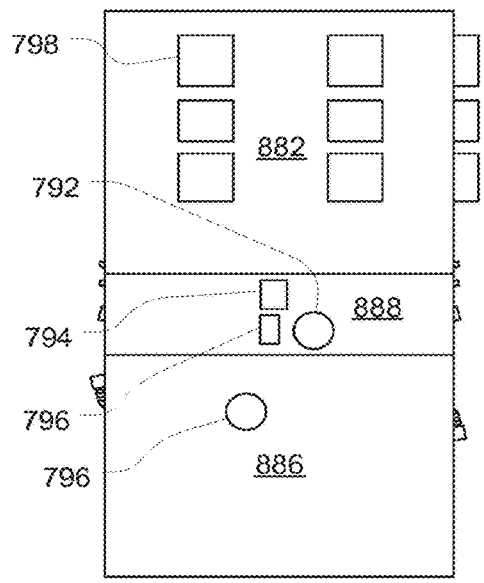

FIGS. 9c and 9d shows three wall modules for a modular wall system essentially as discussed above illustrating internal features and external features, respectively. Three modules are shown including a ductwork module 882 carrying a low temperature exhaust duct 896, a high temperature exhaust duct 894, and an ambient outside air duct 898. Each duct 894, 896, and 898 has a collar 885 which can be used to connected it to a mating end such as end 885 of an aligned duct to carry flow to adjacent modules. Removable blanks such as indicated at 887 can be provided to permit the connection of the ducts 894, 896, and 898 through blanks 798 in the module 882 to external appliances such as exhaust hoods, furnaces devices requiring fresh combustion air, high temperature exhaust such as furnace flue, air curtain requiring fresh air, etc.

The three modules also include a services module 888 which carries other services which may include, for example, a data channel 782, an electrical supply 778, and a water supply 776. The data channel 782 has a connector 776 that interfaces with an external interface module 796 that can be connected to equipment such as appliances, sensors, controllers, data terminals, etc. The electrical supply 778 has a connector that interfaces with an external interface module 794, which may include an electrical utility box and outlet. The water supply 776 has a connector 772 that can connect to external appliances or terminal devices such as faucets. Connecting tubing can be run through a cutout 792 temporarily protected by a removable blank (also shown at 792).

Flexible portions of the data channel 782, electrical supply 778, and water supply 776, for example as indicated at 768 and 758 are shown. Each flexible portion has a corresponding mating connector 752 and 762 to connect with a component of an adjacent module (not shown). The flexibility of the flexible portions allows the connections to be made while permitting the modules to be placed immediately adjacent one another. The flexible portions with mating connectors illustrates one method of permitting connections to be made between adjacent devices, but other methods could be used, for example openable panels (not shown) may be provided at adjoining portions of the modules to permit the interconnection of loosely held data channel 782, electrical supply 778, and water supply 776 with the modules in immediate adjacent relationship.

It is contemplated that the connectors 772, 776, and 774 can be used or unused in a given module so that data channel 782, electrical supply 778, and water supply 776 can convey service to adjacent data channel 782, electrical supply 778, and water supply 776 without any connections at the particular module 888.

Although one each of a data channel 782, electrical supply 778, and water supply 776 are illustrated, it possible to provide more than one of each. In addition, other services may be provided with suitable connectors. For example, liquid heat transfer media at various temperatures may be conveyed through suitable channels and connectors provided for interfacing with heat exchangers. These may include hot and cold heat transfer media for delivery of heat or cooling or for recovery and/or transport of the same.

Similarly a drainage module 886 contains one or more drainage service conduits 757 with flexible portions 756 and connectors 754. One or more removable blanks 796 provide access to a connector 759. The drainage module provides service for devices such as sinks, dishwashers, grease cleaning components of exhaust hoods, etc.

Figure 10:
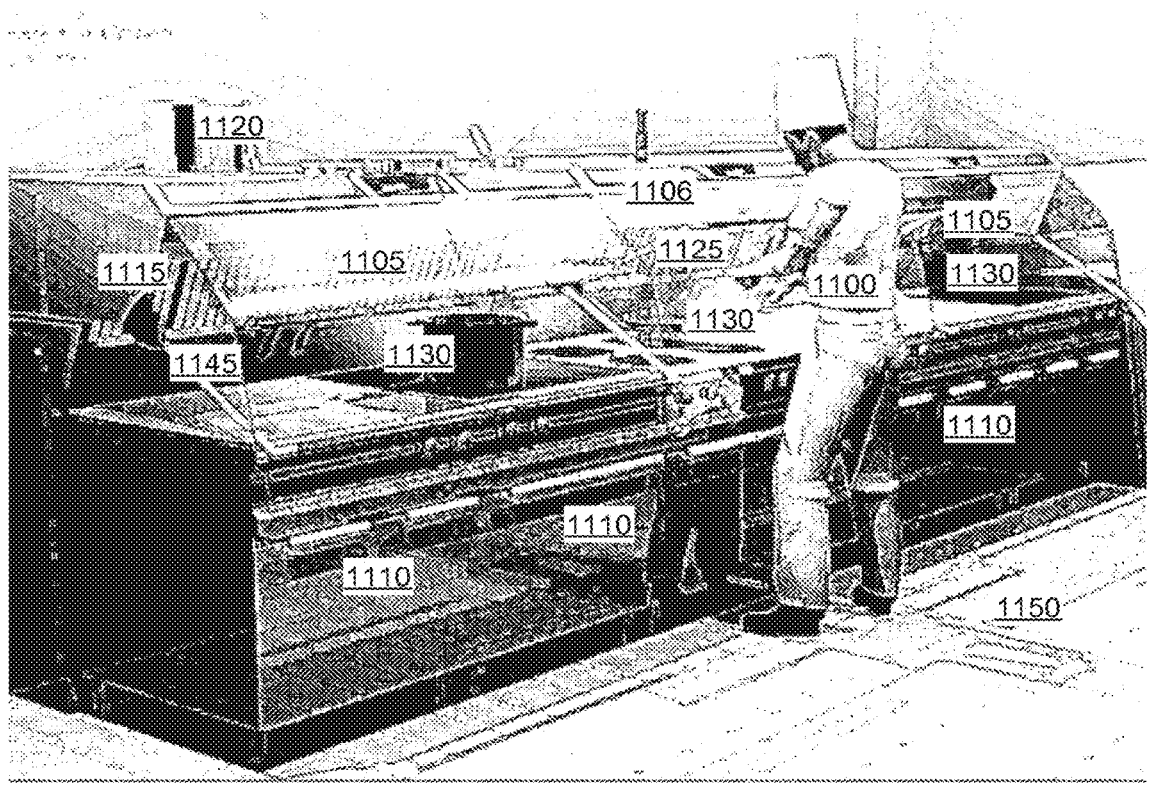
FIG. 10 is a three-dimensional view of a close coupled appliance lineup with has separate shrouds enclosing various cooking operations.

Referring to FIG. 10, an array of cooking appliances 1110 with at least some having heat and fume generating cooking components such as burners, grills, etc. 1130 are protected by movable shrouds 1105/1106. Two shrouds 1105 are shown in a closed position and one 1106 is shown in an open position. In the open position, indicated at 1106, the access is provided to a cook 1100. The shrouds may be of clear material such as temperature tolerant plastic or glass. Preferably the material is opaque to infrared radiation to reduce heat loss to the occupied space 1150 surrounding the cooking appliances 1110 and cooking components 1130. In the open position, the shroud 1106 may be shaped such that it partially intervenes in a line of sight of the cook 1100 to protect the cooks face from radiant heat. This may be better seen in further views discussed below.

The shrouds substantially or fully enclose the cooking/heat sources 1130 when closed, reducing convective and radiant heat loss to the conditioned space 1150. The shrouds 1105/1106 can be selectively raised to allow access. Each movable shroud may have sides 1145 to ensure that when one of two adjacent shrouds 1106 is opened and another 1105 remains closed, heat is not lost through an otherwise open side area. Thus, each shroud 1105/1106 may define a fully enclosed cover isolating the heat sources of adjacent appliances 1110. The isolation also prevents cross-contamination, such as if heavy grease smoke from a grill were to invade a burner area where something was being sautéed.

When a shroud 1105 is closed, the exhaust volume may be minimal while ensuring complete containment of pollutants. This ensures that occupants and cooking pollutants are completely separated. In addition, it prevents contamination of foods by pollutants generated by cooks and other activities in the occupied space. When a shroud such as 1106 is opened, the volume of exhaust may be increased to compensate for the propensity of smoke to escape larger open areas (due to, for example, turbulent scouring) thereby to ensure that contaminants do not escape. Exhaust volume may be regulated by providing a constant low negative pressure such that the shroud 1105/1106 itself regulates the exhaust flow, reducing the volume of exhaust when closed and increasing it when open. Alternatively, the opening and closing may be detected and the exhaust volume regulated accordingly.

In some embodiments, the shroud is controlled automatically, for example by a proximity sensor or a timer set to open the shroud after the lapse of a period of time before some regular operation must be performed, such as flipping hamburgers. Still other alternatives include sensor activation of a shroud-lifting motor, such as radiant temperature sensing. In other embodiments, the shroud is manually controlled. It may spring compensated to make it easier to operate or a manually activated motor may be provided.

In the manner described, the flow through a section where the shroud is closed 1105 can be reduced to a minimal or zero airflow while the airflow through a section where the shroud is open 1106 can be increased accordingly to provide sufficient removal of the heat and contaminants for those sections. When the shroud is in the closed position 1105 it protects the personnel 1100 from exposure to heat, grease, smoke, or other contaminants produced by the cooking/heat source. The shroud 1105/1106 also decreases the radiation load from the cooking appliance/heat source 1130 into the kitchen space resulting in cooler space temperatures. These cooler temperatures allow for a higher level of comfort for the personnel 1100 thereby increasing productivity and maximizing profit for a restaurant.

Furthermore, by closing the shroud 1105 the type of cooking performed by a cooking appliance/heat source 1130 may be altered. Examples of this might be a cooking appliance/heat source which operates as a griddle when the shroud is open 1106 but as a steamer or pressure cooker when the shroud is closed 1105 by trapping all the steam produced from cooking within the enclosed area defined by the sides 1145 and top of the shroud 1105. The airflow is removed by being exhausted through a filter 1125 and plenum section 1115 and through an exhaust duct 1120 located on the side, back or top of the unit. Each module may have its own exhaust plenum 1115 and duct 1120 or these may be combined into a single plenum 1115 and duct 1120 or any combination thereof. Underneath the cooking appliances/heat source 1130 area other appliances may be installed 1110 such as ovens or this area may be used for storage.

The plenum may house heat exchangers, duct couplings for exchange of modular cooking components, depth-loading filters, electrostatic precipitators, ultra-violet lamps or other forms of ozone generators. In a preferred embodiment, heat is recovered from high temperature fumes, such as may be emitted by a gas heated oven or fryer, for example. Some fume streams may carry grease smoke. Preferably such are treated with ultra-violet lamps to convert the sticky smoke particles into ash by fracturing the long chain organic molecules using ozone generated by the lamps. Such treatment may allow heat exchangers to be used without excessive fouling problems.

If ultra-violet lamps are used, the ozone generated by them could also be used to sterilize cooking surfaces. For example, the airflow may be reversed at night so ozone-laden air flowed from the duct 1120 into the space inside the canopy or into the kitchen space therearound, if the shroud is in the open position 1106. This may have the effect of disinfecting the kitchen space while personnel were not present, such as at night or when the facility was closed. With the shroud 1105 in the closed position, the ultraviolet lamps could be turned on and just disinfect and clean grease from the cooking appliances/heat sources 1130. In yet another alternative, the filter housing surface could be lowered automatically allowing ultra-violet light to escape generating ozone remotely from the lamps.

The shrouds may also increase the effectiveness of fire suppression equipment by concentrating treatment near the hot source likely to host the fire. If a fire suppression system is provided within the shroud interior space, such as chemical or water spray, the shroud may help to concentrate the fire suppressant near the fire. The fire suppression system in it could be located above the grease extracting filters 1125 or at some other location within the shroud 1105/1106 interior space. As part of the suppressant system operation, an open shroud 1106 may be automatically closed as indicated at 1106.

Figure 11A:
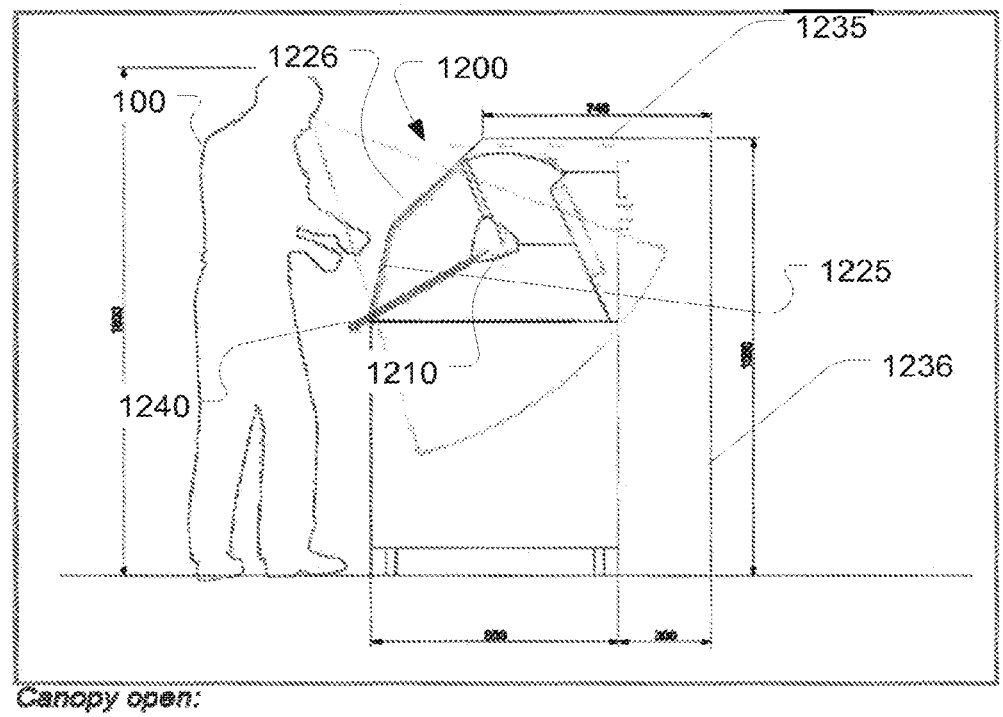
FIGS. 11A and 11B is a cross sectional view of a canopy that can be rotated up for access to the cooking appliances.
Figure 11B:
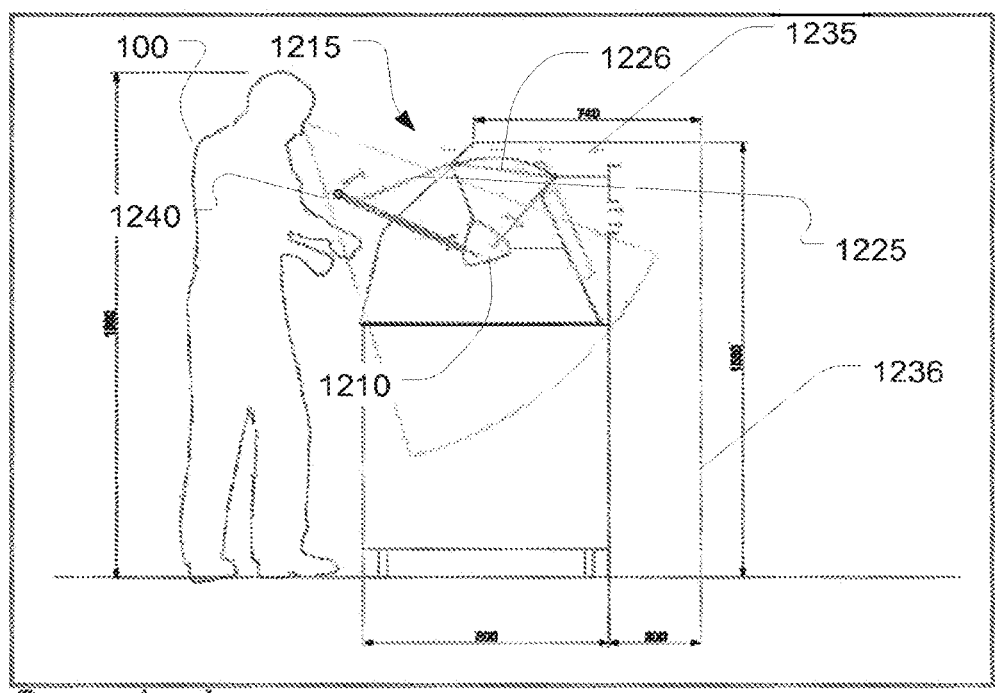

Referring to FIGS. 11A and 11B, a cross sectional view of one embodiment shows a shroud 1200 in closed and open positions at 1200 and 1215, respectively. In the current embodiment, the shroud rotates around a hinge 1210 to allow the shroud 1200 to be open and closed. A flat lower portion 1225 remains in a line of sight of cook 1100 to block heat radiation. The flatness helps to avoid any distortion of the view by refraction. The upper portion 1226. As also indicated at 1235, supply air may be conveyed through a rear plenum 1236 to flow toward the cook 1100. Although not shown, the exhaust and supply streams may be supplied by separate plenums within the housing indicated at 1236. A handle 1240 may be provided to open and close the shroud 1200/1215.

Figure 12A:
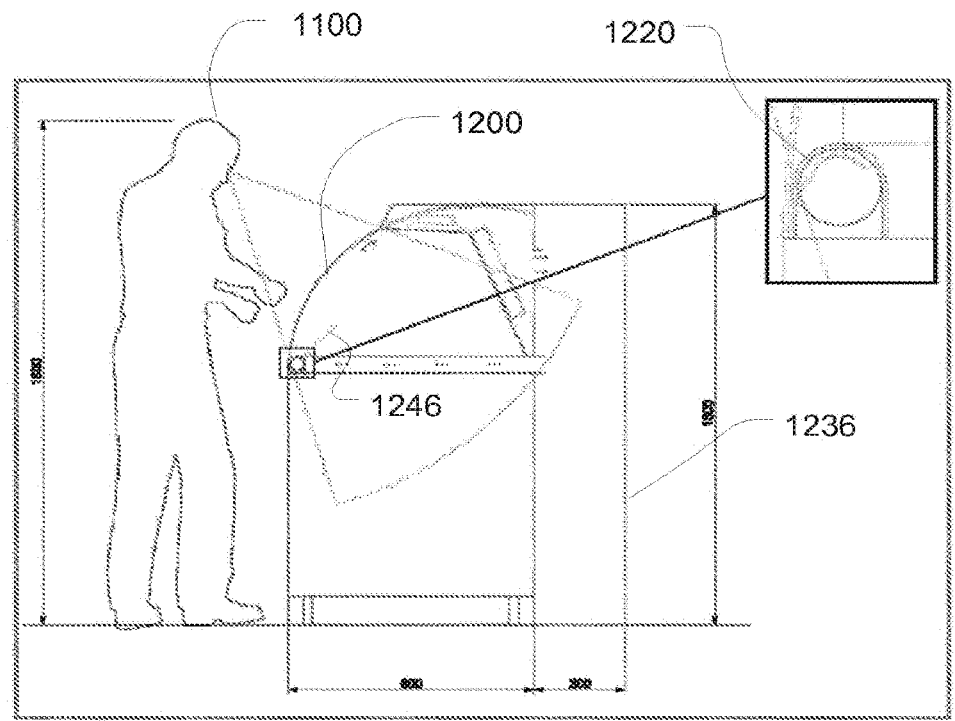
FIGS. 12A and 12B is a cross sectional view of another embodiment that incorporates air jets to keep the cooking shroud clean and assist in capturing the cooking effluent when the shroud is raised.
Figure 12B:
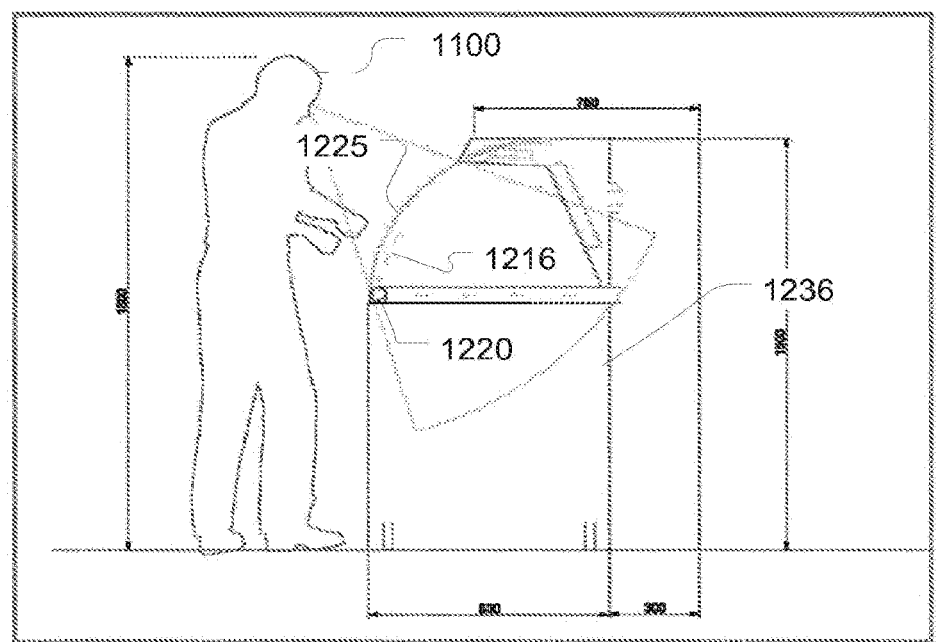

Referring to FIGS. 12A and 12B, a cross sectional view of a different embodiment in which jets of air 1246 are used to reduce the airflow requirements with the open shroud 1200. The air is brought in through the supply air portion of the plenum housing 1236 and discharged through rotating plenum 1220. With the shroud in the closed position 1225 the plenum 1200 is rotated so that the jets 1216 are directed along the inside face of the shroud 1225 in a tangential direction to the interior surface of the shroud, which in the present embodiment is a monotonically curved surface. The jets 1216 can have several benefits including keeping the shroud cover 1225 clean from grease or other substances when it is in the closed position. Also, it may keep the shroud from getting very hot thereby avoiding causing skin burns. In the open position, the direction of the jet is changed as indicated at 1246 to position that, by entrainment, helps to capture and guide turbulent smoke puffs into the exhaust stream thereby to ensure capture and containment of smoke and other pollutants.

Figure 13A:
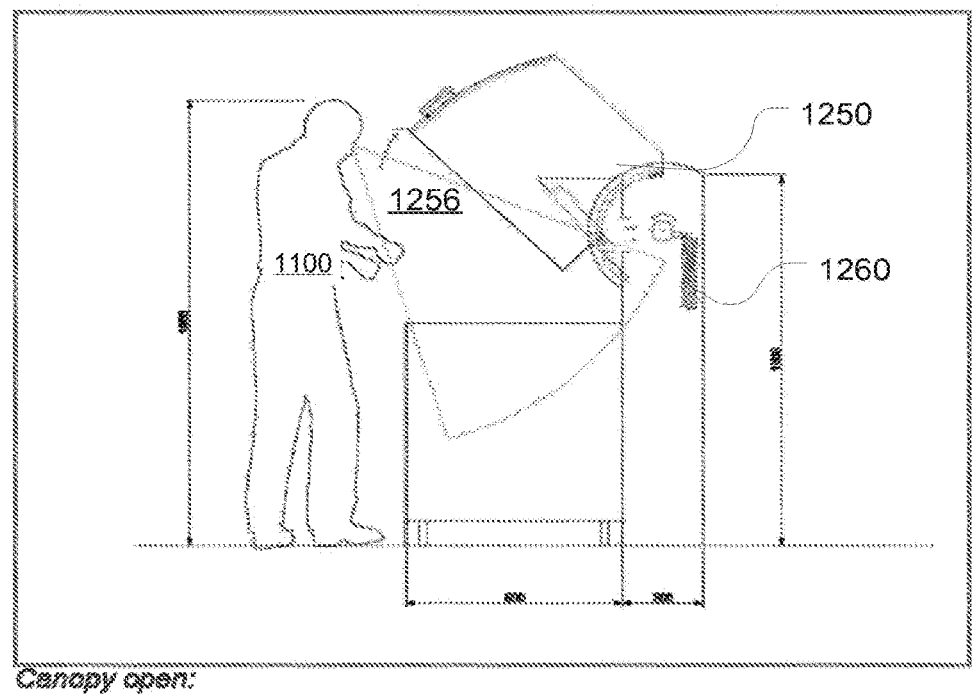
FIGS. 13A and 13B is a cross sectional view of another embodiment where the shroud is integrated with the top of the hood and the entire assembly can be raised with the assistance of a spring system.
Figure 13B:
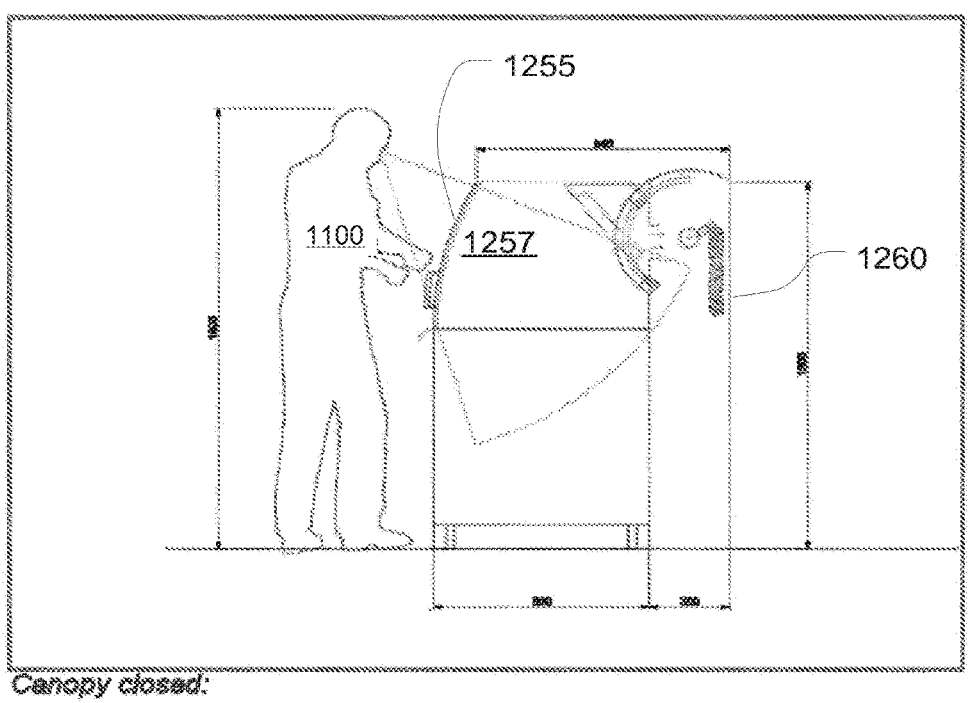

Referring to FIGS. 13A and 13B, a cross sectional view of an alternate embodiment of the shroud 1250 is shown in which the entire shroud rotates between closed position 1255 and open position 1250. In a manual mechanical embodiment, the weight of the shroud 1255/1250 may be compensated using springs 1260 or actuated a motor (replacing springs 1260 with a linear actuator). Means of actuation are not limited. The spring 1260 as illustrated and may be replaced by or include linear motors, pneumatics, hydraulics, counter balances, or similar mechanisms.

Figure 14A:
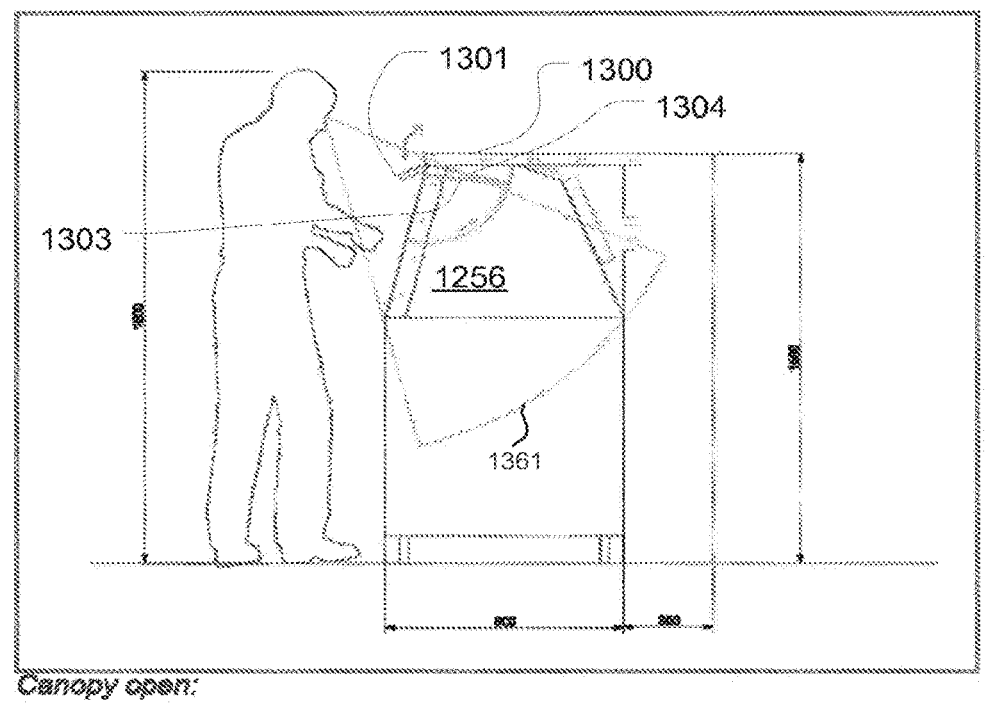
FIGS. 14A and 14B is a cross sectional view of another embodiment where the shroud folds and bends inwardly to create clearance for an operator.
Figure 14B:
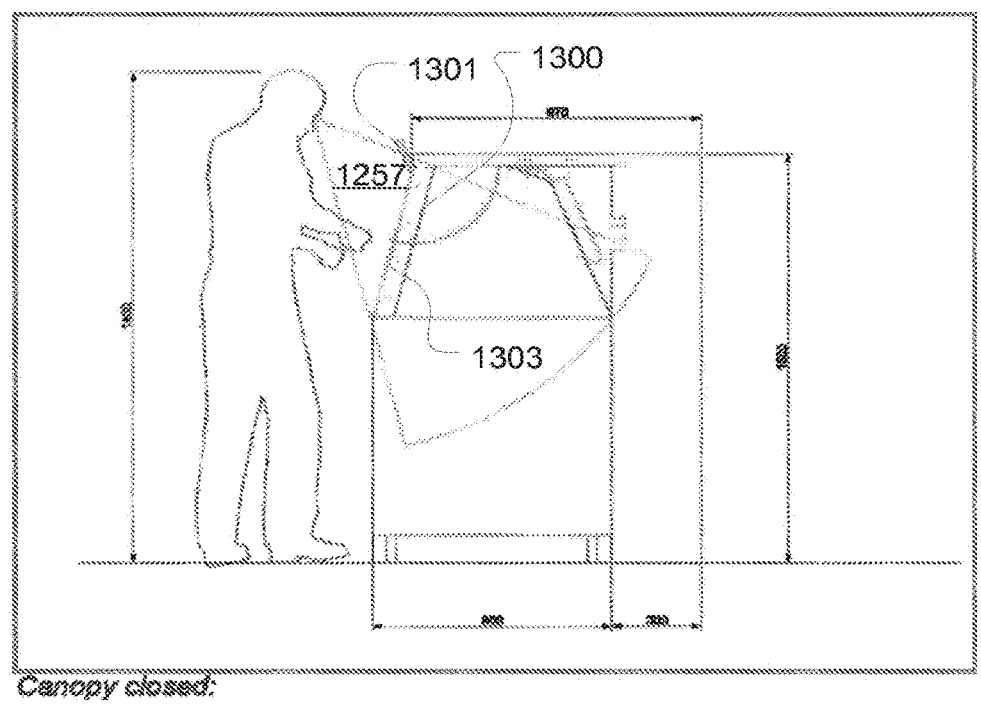

Referring to FIGS. 14A and 14B, a cross sectional view of an embodiment where the front of the shroud forms a bi-fold front element 1303/1304 that folds into the cooking area as shown. The front is shown folded in an open position at 1304 and unfolded in a closed position at 1303. In this embodiment, the closed shroud 1300 folds at a hinged portion into a horizontal position. Opening and closing may be facilitated by a lever 1301. The angle of view is indicated 1361 when the shroud is in the open position 1256 as well as the closed position 1257, assuming the shroud 1360 is of a transparent material. An alternative in this embodiment is one in which only the cover 1304 is present and the front opening is only partly covered when the cover 1304 is in the lowered position of FIG. 14B.

Figure 15A:
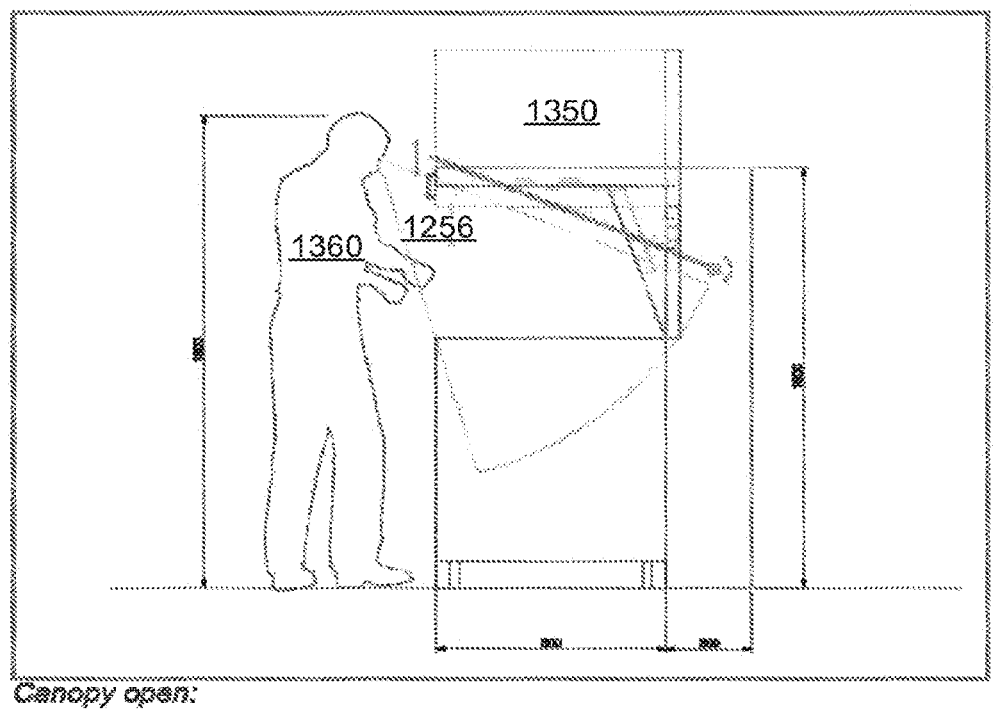
FIGS. 15A and 15B is a cross sectional view of another embodiment where the entire shroud can be lifted vertically upward for the chef to access the cooking appliance.
Figure 15B:
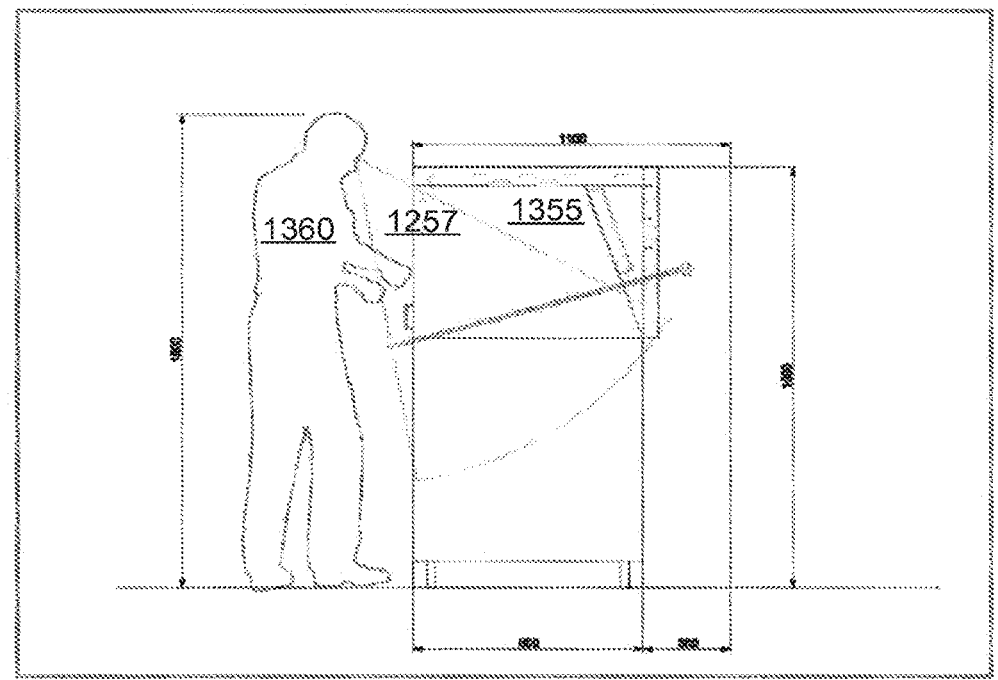

Referring to FIGS. 15A and 15B, a cross sectional view of an embodiment is shown in which the shroud 1360 moves vertically to the open 1350 or closed 1355 position. Such operation may be provided by motors or weight compensating mechanisms (not shown). The angle of view is indicated 1361 when the shroud is in the open position 1256 as well as the closed position 1257, assuming the shroud 1360 is of a transparent material.

Figure 16:
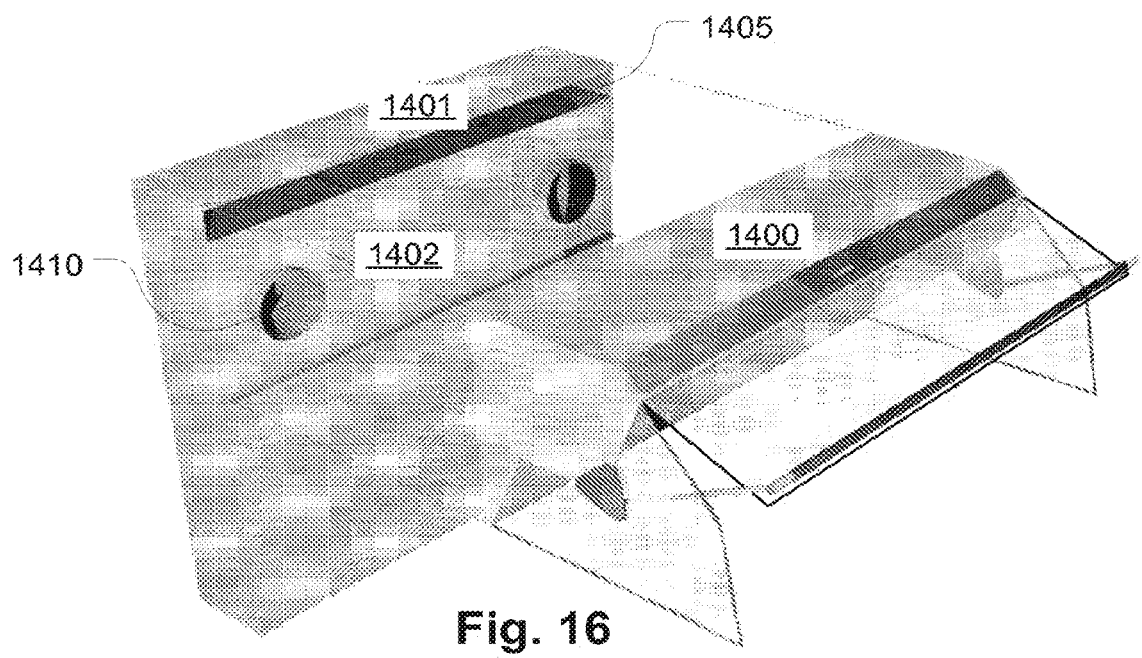
FIG. 16 is an embodiment showing a connection between the shroud and filter assembly to the exhaust system.

Referring to FIG. 16, a three dimensional view of one embodiment which shows how supply air from a supply plenum 1401 could be coupled to a supply passage integrated into the shroud section indicated at 1400 via a supply coupling 1405 located above an exhaust plenum 1402. An exhaust plenum may be connected to a shroud section filter plenum 1400 through duct couplings 1410. The exhaust and supply plenums 1401 and 1402 may be permanently affixed to a facility and appliances with shrouds (or just the shrouds) connected to them. Standard spacing's and configurations may be provided to allow easy replacement or substitution of shrouds or shrouded appliances. The exhaust and supply plenums may continue beyond what is shown to provide for the supply and exhaust requirements of multiple shrouds or shrouded appliances.

Figure 17:
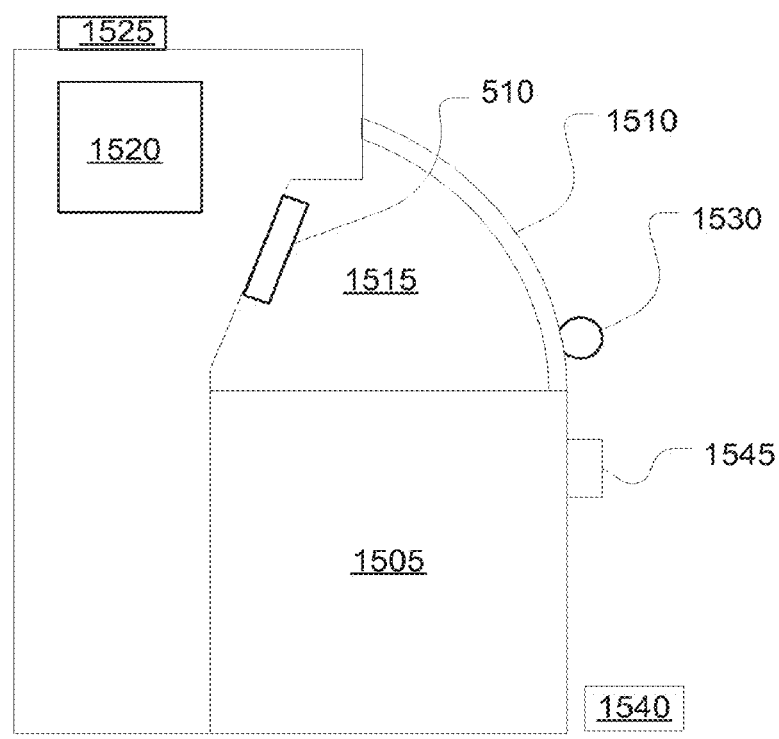
FIG. 17 is a cross sectional view of an embodiment showing the integration of the shroud, appliance, and hood assemblies.

Referring to FIG. 17, a cross sectional view of an embodiment illustrates various features discussed within the instant specification. The assembly is comprised of an appliance 1505 enclosed by a shroud 1510 on top and on the ends 1515. Exhaust is pulled through a filter assembly 1515 and can exit the rear plenum through an exhaust duct 1520 on the side of the unit, the top of the unit 1525 or at another location. The shroud 1510 can be operated by personnel using a handle mechanism 1530 or an alternate means such as a foot operated pedal 1540, proximity sensor 1545, or a timer which raises the shroud 1510 when cooking is completed.

Figure 18A:
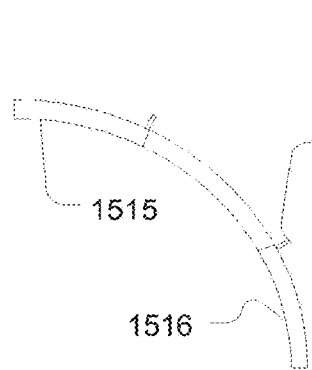
FIGS. 18A-18D shows cross sectional views of alternate embodiments for the shroud operation.
Figure 18B:
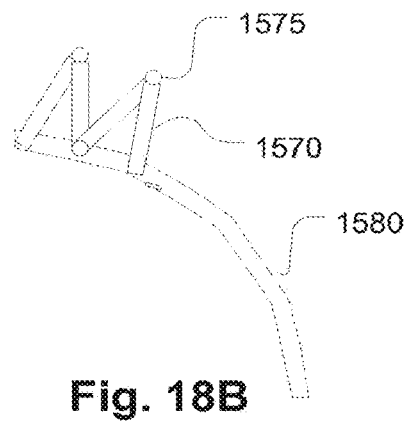
Figure 18C:
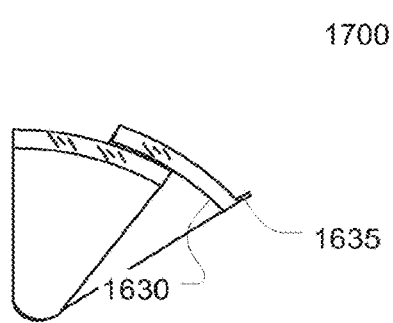
Figure 18D:
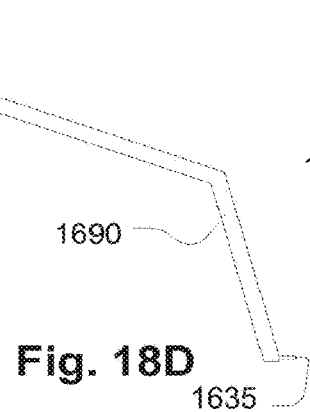

Referring to FIGS. 18A through 18D, alternate embodiments of how a shroud could operate are displayed. FIG. 18A shows the shroud 1520 which splits into two portions, the upper portion of the shroud 1515 recesses into top of the plenum assembly and the lower section of shroud 1516 recesses underneath or in front of the cooking appliances. A handle 1520 provides a means for personnel to move the shroud 1516. FIG. 18B is a cross sectional view of another embodiment of the shroud configuration. In this embodiment, the shroud 1570 has bi-folds or louvers which allow it to fold up into a compact space. In this embodiment pins 1575 are shown as a means of allowing the shroud 1570 to bend. Alternatively, this could be achieved by other means such as hinges or flexible connectors. In this embodiment, a track 1580 provides a means to guide the shroud 1570 into place. FIG. 18C is a cross sectional view of a shroud embodiment in which the shroud is comprised of several panels 1630 which, when recesses, can overlap each other to minimize or eliminate the need of having storage space for the shroud 1630 when it is open. A handle 1635 can provide a means for personnel to open the shroud 1630 manually. FIG. 18D is a cross sectional view of a shroud consisting of two flat sections which intersect to form a single shroud 1690 and rotate around a pivot point 1700. An alternate number of panels could be used to form the shroud 1690. In order to minimize or eliminate accumulation of grease or other substances on the shroud 1690, the angle of the shroud 1690 from horizontal needs to be optimized. Factors that can impact this angle include the type of grease used in cooking applications, the internal and external temperatures of the shroud 1690, and the quantity of steam present in the enclosure. A trough can be located at the bottom of the shroud 1690 or at the intersection of the shroud and cooking appliance/heat source to accumulate any grease or other substances. In all the embodiments of FIGS. 18A to 18D a fixed or movable side section may be used to provide complete enclosure of the shroud interior.

Figure 19:
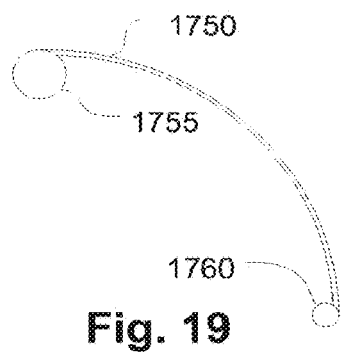
FIG. 19 shows cross sectional views of alternative types shroud containment.

Referring to FIG. 19, a cross sectional view of an embodiment in which the shroud 1750 is manufactured from a flexible material that can be rolled up, such as cloth, plastics, metal or plastic rods is shown. In this embodiment there would be a feed roller 1755 which stores the material and an uptake roller 1760. The shroud 1750 could be manufactured from transparent or translucent materials.

Figure 20:
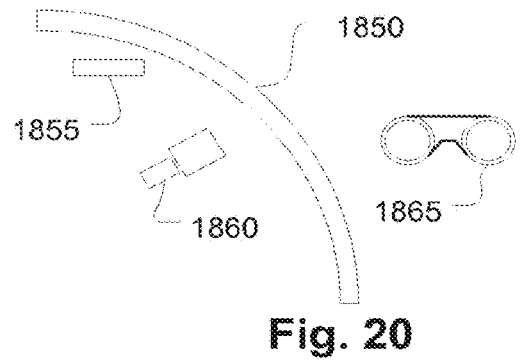
FIG. 20 shows a cross sectional view of means for a chef to detect cooking for use with a non-clear type of shroud.

Referring to FIG. 20, an embodiment is shown where the personnel does not have a visible line of sight to the cooking appliances/heat source through the shroud 1850. In this embodiment a camera 1860 is used in conjunction with goggles 1865 to allow the personnel to observe the cooking process without opening the shroud 1850. Alternatively, an infrared sensor 1855 could be used to detect when cooking has been completed. Alternate types of sensors, such as sound or chemical could be used to detect when cooking has been completed.

Figure 21A:
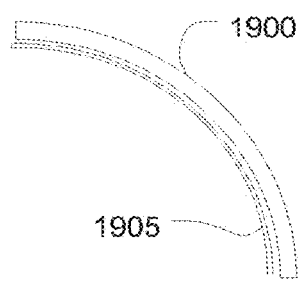
FIGS. 21A and 21B shows cross sectional views of means of cleaning the shroud to remove grease and other cooking byproducts.
Figure 21B:
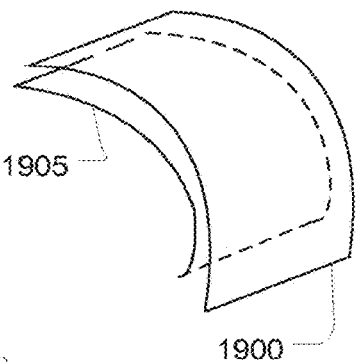
Figure 22:
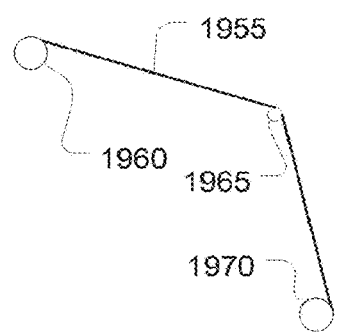
FIG. 22 shows a cross-sectional view of a shroud with a replaceable film which is dispensed and rolled up in place.

Referring to FIGS. 21A and 21B, a cross sectional view and three dimensional view of a mechanism for maintaining a clean shroud cover are shown. In this embodiment, a removable film 1905 is attached to the inside of the shroud 1900. When the film 1905 becomes dirty it can be peeled off revealing a clean shroud 1900. A new film 1900 could then be installed on the inside of the shroud 1900 prior to using the cooking appliance/heat source. Alternatively, multiple adjacent layers of film may be installed at a single time and peeled away successively until used up. FIG. 22 shows another view of the film application where the film 1955, is dispensed by a feed roller 1960 and collected by an uptake roller 1970. In this embodiment, retaining rollers 1965 are used so that the film follows the inside contour of the shroud.

Figure 23:
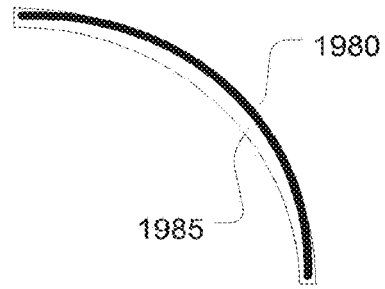
FIG. 23 shows a cross sectional view of a shroud which is insulated with either an air space or insulation material to keep the outside of the shroud cool.

Referring to FIG. 23, a cross sectional view of an embodiment of an insulated shroud is shown. In this embodiment a shroud 1980 is insulated with an air gap void 1985 to reduce the outer surface temperature. An alternate embodiment would be to fill air gap void 1985 with another stationary or recirculating fluid to cool down the shroud.

Figure 24A:
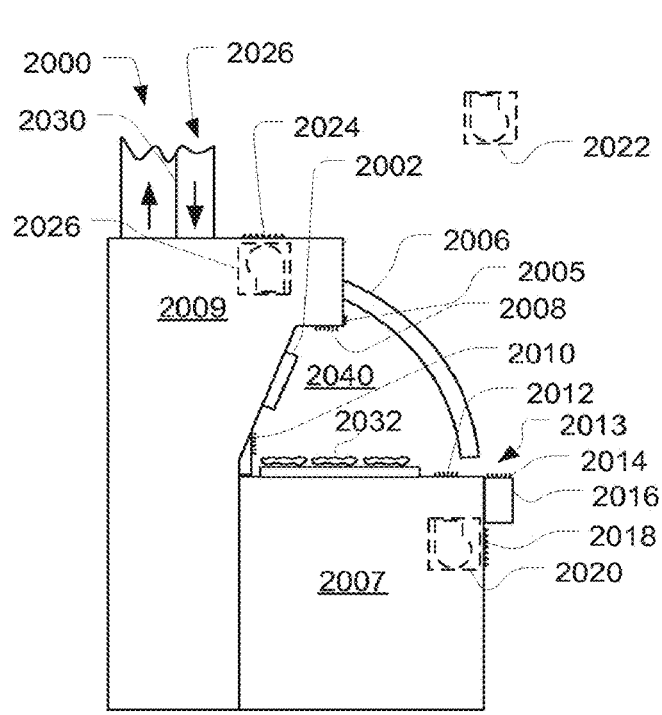
FIG. 24A is a side, partial cutaway, view of a grill with a hood and various locations of intake and discharge registers for conditioned and make-up air according to respective embodiments.

FIG. 24A shows a cooking appliance 2007 and an exhaust module 2009 which make up a system combination 2000 and the locations of various intake and discharge registers that operate in conjunction with the exhaust system. Each of the discharge registers does one or more of the following: aids in the capture and containment of fumes, keeps a shroud 2006 clean, and/or continuously refreshes the air immediately around food to keep it from picking up too much smoke residue. The air provided to the discharge registers may be obtained from either or both of conditioned air from the building in which the combination 2000 is located and a source of make-up air 2030 which may be obtained from outside the conditioned space.

Fumes from the cooking appliance 2007 and food being cooked 2032 are drawn into an exhaust intake 2002 which draws air and fumes from an interior space 2040 defined by the cooking appliance 2007, the exhaust module 2009, and the shroud 2006. The exhaust intake 2002 preferably has a grease filter (not shown separately).

Air that replaces exhausted air and fumes from the interior space 2040 can be supplied to the interior space 2040 through a gap 2013 in the shroud 2006. The gap 2013, in an embodiment, is adjustable to permit access to food 2032 or cooking vessels and/or equipment located in the interior space 2040. In further embodiments, the air gap 2013 is adjustable in small degrees to regulate the flow of air into the interior space 2040.

Air that replaces exhausted air and fumes from the interior space 2040 can be supplied to the interior space 2040 can, in addition or alternatively, in other embodiments is supplied through one or more discharge registers 2005, 2008, 2010, 2012, 2014. The air provided to these discharge registers 2005, 2008, 2010, 2012, 2014 can be obtained from the conditioned space through intake registers which are placed appropriately, for example as indicated at 2018 and 2024. One or more fan units are provided as required, for example as indicated at 2026 and 2020. Also fan units can be located remotely from the cooking appliance 2007 and the exhaust module 2009, as illustrated at 2022. Fan units can be eliminated in embodiments if the exhaust flow is sufficient to overcome resistance required to draw replacement air into the interior space 2040.

Figure 24B:
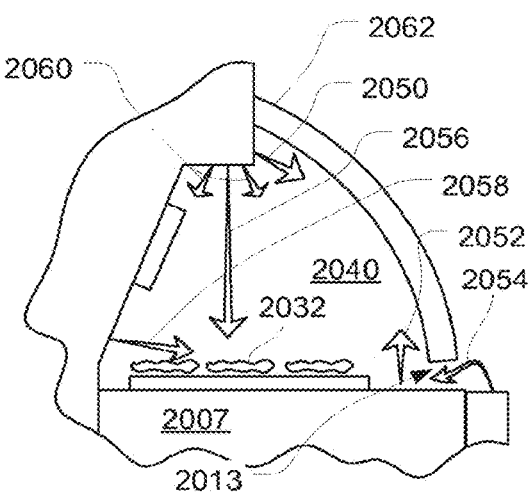
FIG. 24B illustrates the air flow patterns which can be obtained according to the various embodiments of FIG. 24A.

Referring now to FIG. 24B, one or more of the discharge and intake registers described with reference to FIG. 24A can be used to generate one or more of the jets 2050, 2060, 2056, 2058, and 2052 or diffuse, low-velocity flows of replacement air into the interior space 2040. A vertical jet 2056, for example, is of sufficient velocity and thickness to "wash" the surface of the food 2032, thereby causing fumes to move away from the food 2032 and prevent or reduce the condensation or precipitation of vapor or aerosols in the smoke on the food 2032. A washing effect can also be obtained by directing a flow from the back of the interior space as indicated at 2058. In respective embodiments, either and both of flows 2050 from the top, and 2052 from the bottom, are directed at the shroud 2062 to help keep it clean. A jet 2054 directed upwardly from outside the interior space is drawn in through a gap 2013 between the shroud 2062 and the appliance 2007. The gap 2013 is open in some embodiments and closed in others, unless the shroud 2062 is opened to provide access to the food 2032.

Figure 25A:
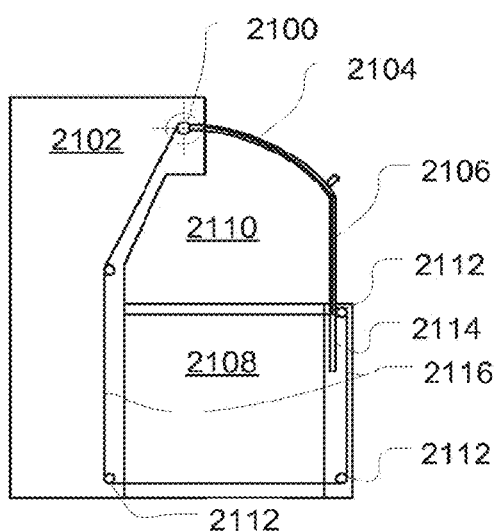
FIGS. 25A-25D illustrate various mechanisms for providing a two-part shroud.
Figure 25B:
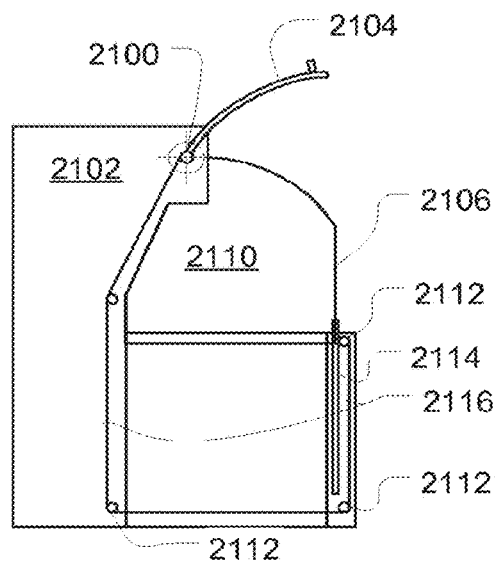

Referring now to FIG. 25A, an exhaust module 2102 has a movable shroud cover 2104 which pivots about a cable drive 2100 which connects the shroud cover through a cable 2116 to a movable shroud partition 2114. The shroud cover 2102, the shroud partition 2106, and a side partition 2106 together enclose the interior space 2110 over an appliance 2108. As described elsewhere, various mechanisms can be provided to bring replacement air into the interior space 2110. The cable 2116 is guided by pulleys 2112 and there may be multiple sets along the depth of the figure which are not shown. As the shroud cover 2104 is pivoted into the position shown in FIG. 25B, the cable drive 2100 takes up the cable 2116 and paying it out where it attaches to the shroud partition 2114, causing the latter to drop into the position shown in FIG. 25B. The configuration shown permits the front and top areas of the shroud to be cleared with a relatively short displacement of the shroud cover 2104. The mechanism used can be motor-driven. The cable drive can be any suitable ratio metric drive, such as a planetary gear train suitable for creating sufficient take-up and payout over the angular displacement of the shroud cover 2104 required.

Figure 25C:
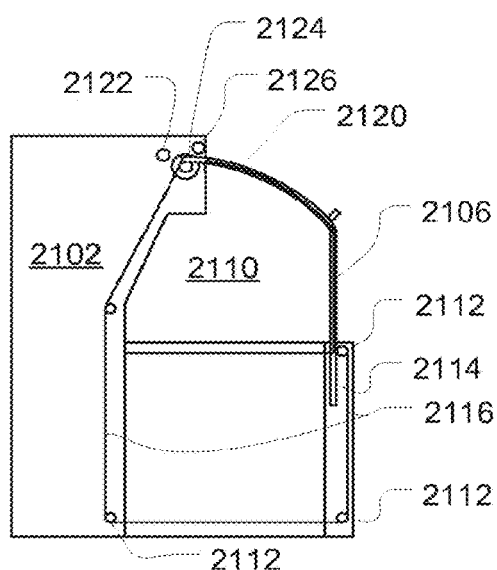
Figure 25D:
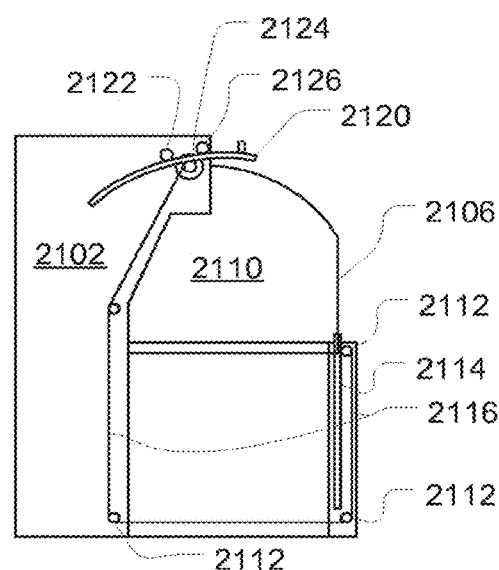

FIG. 25C shows an alternative arrangement in which a shroud cover 2120 is moved rearwardly as shown in FIG. 25D instead of pivoting upwardly. Any suitable device can be used to provide for the motion of the shroud partition 2106 and the cover 2120. For example, rollers 2122, 2124, and a rack (not shown) attached to the cover can engage a suitable cable drive 2126.

In various embodiment the discharge registers 2005, 2008, 2010, 2012, 2014 are configured to create jets of different configuration to regulate the flow of air into and/or within the interior space 2040. Register 2008 can create a downward-projecting jet that washes the upper surface of food 2032. Such a jet mitigates or eliminates the settling of tar and/or other aerosols onto the food 2032. Such materials can adversely affect the taste of food. For example, food can taste differently depending on whether it is cooked on an open grill or a covered grilled, which is a result of the settling of the materials in smoke on the food. By directing replacement air into the space immediately surrounding the food 2032, the settling of such materials can be reduced or eliminated.

To some extent, such settling may be desirable so that, in an alternative embodiment, the flow of the jet emitted from the discharge register 2008 can be adjusted to reduce its velocity such that its energy dissipates to an extent before it arrives the region immediately surrounding the food 2032. Vanes of the discharge grill 2008 can therefore be made adjustable so that they fan out, to cause the air to dissipate, to an adjustable extent, or to be arranged in parallel to form a narrow jet. Other ways of forming diffuse or projecting jets can be used instead of the vane embodiment described. For example, diffuser screens can be moved into and out of a projected stream or turbulators can opened or closed in a projected stream. Many such devices are known and used in various settings for ventilation so the topic is not discussed further here.

Preferably, the foregoing exhaust modules 2009 and 2102 are configured to be connected to the modular wall system described with reference to FIGS. 8*a*-8*d*, 9*a* and 9*b*.

While the present invention has been disclosed with reference to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

The invention claimed is:

1. An exhaust hood, comprising:
an exhaust inlet;
a shroud having a lower edge extending in a first direction and being movable;
the shroud being configured to define an enclosed space over and adjacent a cooking surface, the enclosed space being in communication with the exhaust inlet;
the shroud being movable to a first position providing clearance between the cooking surface and the shroud lower edge and a second position providing less clearance than the clearance provided by the first position;
a first discharge register positioned adjacent the cooking surface, inside of the enclosed space, and configured to emit a vertical jet at said lower edge, the vertical jet aimed upwardly and directed along an inside of the shroud toward a second discharge register, when the shroud is in the second position, said vertical jet being in the enclosed space; and
the second discharge register positioned adjacent a top of said shroud and configured to emit at least a horizontal jet at the top of said shroud, the horizontal jet directed along the inside of the shroud toward the first discharge register, when the shroud is in the second position, said horizontal jet being in the enclosed space.

2. The exhaust hood of claim 1, further comprising:
a third discharge register positioned above the cooking surface and configured to emit a jet horizontally over the cooking surface toward the lower edge of the shroud, when the shroud is in the second position.

3. The exhaust hood of claim 2, wherein
the second discharge register is further configured to emit a jet toward the third discharge register.

4. The exhaust hood of claim 1, wherein the shroud has a transparent portion.

5. The exhaust hood of claim 1, wherein the shroud has a transparent portion and the transparent portion is located such that a standing person can view at least a portion of the cooking surface through the transparent portion when the shroud is in the first position.

6. The exhaust hood of claim 1, wherein the shroud has a transparent portion and the transparent portion is located such that a standing person can view at least a portion of the cooking surface through the transparent portion when the shroud is in the first and second positions.

7. The exhaust hood of claim 1, wherein said vertical and horizontal jets are composed of conditioned air from an ambient space.

8. The exhaust hood of claim 1, further comprising at least one fresh air vent in communication with the enclosed space and configured to form a jet that washes the cooking surface.

9. The exhaust hood of claim 1, wherein
the second discharge register extends in the first direction along the top of the shroud.

10. The exhaust hood of claim 1, wherein
the second discharge register is further configured to emit a vertical jet downward toward the cooking surface.

\* \* \* \* \*